United States Patent [19]

Pigerol et al.

[11] 4,201,725
[45] May 6, 1980

[54] SECONDARY AMINES

[75] Inventors: Charles Pigerol, Saint-Ouen; Pierre Eymard, Fontaine; Jean-Claude Vernieres, Domene; Jean-Pierre Werbenec, Eysines; Madeleine C. Epse Broll, Le Fontanil, all of France

[73] Assignee: Labaz, Paris, France

[21] Appl. No.: 888,187

[22] Filed: Mar. 20, 1978

Related U.S. Application Data

[63] Continuation-in-part of Ser. No. 876,200, Feb. 9, 1978, abandoned, which is a continuation of Ser. No. 707,898, Jul. 22, 1976, abandoned, which is a continuation-in-part of Ser. No. 577,732, May 15, 1975, Pat. No. 4,026,925.

[30] Foreign Application Priority Data

May 20, 1974 [BE] Belgium ............................ 144519

[51] Int. Cl.² .................... C07C 87/08; A61K 31/13
[52] U.S. Cl. ........................... 260/583 H; 260/501.1; 260/561 N; 260/583 R; 260/583 J; 260/583 L; 260/583 K; 260/585 A; 424/325; 560/172; 562/598
[58] Field of Search ............ 260/501.1, 583 H, 583 J, 260/583 R

[56] References Cited

U.S. PATENT DOCUMENTS

| | | | |
|---|---|---|---|
| 2,230,752 | 2/1941 | Klavelm et al. | 260/583 R |
| 2,606,923 | 8/1952 | Bortnick | 260/583 R |
| 2,766,285 | 10/1956 | Hennion | 260/583 H |
| 3,067,101 | 12/1962 | Easton et al. | 260/583 H |
| 3,123,646 | 3/1964 | Easton et al. | 260/583 R |
| 3,168,567 | 2/1965 | Easton et al. | 260/583 H |
| 3,413,278 | 11/1968 | Weinrich et al. | 260/583 R |
| 3,574,760 | 4/1971 | Sasaki et al. | 260/583 R |
| 3,644,525 | 2/1972 | Thiele | 260/501.1 |
| 4,026,925 | 5/1977 | Pigerol et al. | 260/501.1 |

FOREIGN PATENT DOCUMENTS

| | | | |
|---|---|---|---|
| 815273 | 11/1974 | Belgium | 260/583 R |
| 517997 | 11/1955 | Canada | 260/583 R |
| 522710 | 3/1956 | Canada | 260/583 R |

OTHER PUBLICATIONS

Kharkevich, "Chem. Absts.", 57, 15755(h), 1962.
Vurtanyan, "Chem. Absts.", 68, 38971(j), 1968.
Iffland et al., "Chem. Absts.", 67, 90340(w), 1967.
Montagne et al., "Chem. Absts.", 40, 5696(b), 1946.
Vejdelek, "Chem. Absts.", 55, 9280(g), 1961.
Lukes, "Chem. Absts.", 52, 4483(d), 1958.
Khorlin et al., "Chem. Absts.", 55, 24538(h), 1961.
Easton et al., "Chem. Absts.", 56, 5818(e), 1962.
Kharkevich, "Chem. Absts.", 75, 47363(j), 1971.
Kitatsuji et al., "Chem. Absts.", 75, 117837(t), 1971.
Sperber et al. J.A.C.S., 71, 3352, 1949.
Hennion et al., J.A.C.S., 75, 4297, 1953.
Ritter et al., J.A.C.S., 70, 4048, 1948.
Henze et al., J. A.C.S., 65, 87, 1943.
Marsh et al., J. Pharm. Exptl. Therap., 98, 300 4 (1950).
Vejdelek et al., Coll. Czech. Chem. Comm., 35, 2810–2814, 1970.

Primary Examiner—Bernard Helfin
Assistant Examiner—G. T. Breitenstein
Attorney, Agent, or Firm—Mason, Kolehmainen, Rathburn & Wyss

[57] ABSTRACT

Methylamine derivatives of the formula:

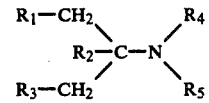

and pharmaceutically acceptable acid addition salts thereof, wherein $R_1$ and $R_3$ each represent a hydrogen atom or a straight- or branched-chain alkyl, alkenyl or alkynyl radical containing from 1 to 6 carbon atoms, $R_2$ represents a straight- or branched-chain alkyl, alkenyl or alkynyl radical containing from 2 to 7 carbon atoms with the proviso that when $R_2$ represents an alkenyl radical of the formula $CH=CH-R_6$ or an alkynyl radical of the formula $C\equiv C-R_6$, in which $R_6$ represents a hydrogen atom or a straight- or branched-chain alkyl radical of 1 to 5 carbon atoms, $R_1$ and $R_3$ each represent an atom of hydrogen or an alkyl radical, $R_4$ and $R_5$, which are the same or different, each respresent a hydrogen atom, a straight- or branched-chain alkyl, alkenyl or alkynyl radical containing from 1 to 5 carbon atoms or an ω-hydroxyalkyl radical containing from 2 to 5 carbon atoms or $R_4$ and $R_5$, when they are taken together represent an alkylene radical containing from 2 to 6 carbon atoms, an alkylidene radical containing from 1 to 5 carbon atoms or the radical $-CH_2-CH_2-O-CH_2-CH_2-$, $R_1$, $R_2$ and $R_3$ being such that the trisubstituted methylamine radical possesses no more than 13 carbon atoms.

They are useful for treating Parkinson's disease and for correcting extra-pyramidal disturbances provoked by neuroleptics.

6 Claims, No Drawings

SECONDARY AMINES

CROSS-REFERENCE TO RELATED APPLICATION

This application is a continuation-in-part of application Ser. No. 876,200 filed Feb. 9, 1978 now abandoned which is a continuation of Ser. No. 707,898 filed July 22, 1976 now abandoned, which is a continuation-in-part of Ser. No. 577,732 filed May 15, 1975, now U.S. Pat. No. 4,026,925 granted May 31, 1977.

The present invention relates to pharmacologically active derivatives of methylamine and their pharmaceutically acceptable acid addition salts as well as to pharmaceutical and veterinary compositions containing the said derivatives and salts.

The invention also concerns processes for preparing the derivatives of the invention and for the preparation of compositions containing them.

The pharmacologically active compounds with which the invention is concerned correspond to the following general formula:

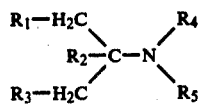

wherein $R_1$ and $R_3$ represent a hydrogen atom or a straight- or branched-chain alkyl, alkenyl or alkynyl radical containing from 1 to 6 carbon atoms, $R_2$ represents a straight- or branched-chain alkyl, alkenyl or alkynyl radical containing from 2 to 7 carbon atoms with the proviso that when $R_2$ represents an alkenyl radical of the formula CH=CH—$R_6$ or an alkynyl radical of the formula C≡C—$R_6$, in which $R_6$ represents a hydrogen atom or a straight- or branched-chain alkyl radical of 1 to 5 carbon atoms, $R_1$ and $R_3$ each represent an atom of hydrogen or an alkyl radical, $R_4$ and $R_5$, which are the same or different, each represent a hydrogen atom, a straight- or branched-chain alkyl, alkenyl or alkynyl radical containing from 1 to 5 carbon atoms or an ω-hydroxyalkyl radical containing from 2 to 5 carbon atoms, or $R_4$ and $R_5$, when they are taken together represent an alkylene radical containing from 2 to 6 carbon atoms, an alkylidene radical containing from 1 to 5 carbon atoms or the radical —CH₂—CH₂—O—CH₂—CH₂—, $R_1$, $R_2$ and $R_3$ being such that the trisubstituted methylamine radical possesses no more than 13 carbon atoms.

The invention also relates to the pharmaceutically acceptable acid addition salts of the compounds of formula I such as the acid addition salts obtained with an inorganic acid, for example, hydrochloric acid, or with an organic acid in which the free carboxyl is attached to a saturated or unsaturated aliphatic radical, or an aromatic or aralkyl radical which may optionally contain a second carboxyl group such as, for example, fumaric acid.

A preferred class of compounds of formula I can be represented by the following general formula:

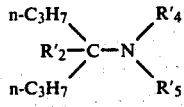

wherein $R'_2$ represents a straight- or branched-chain alkyl group having from 2 to 4 carbon atoms or allyl, $R'_4$ represents hydrogen, methyl, propargyl or 2-hydroxyethyl, $R'_5$ represents hydrogen, methyl, ethyl, n-propyl, isopropyl, allyl, propargyl, 2-hydroxyethyl or 3-hydroxy-n-propyl or $R'_4$ and $R'_5$, when they are taken together, represent a methylene, ethylene, trimethylene, ethylidene or the radical —CH₂CH₂—O—CH₂—CH₂— as well as the pharmaceutically acceptable acid addition salts of these compounds of formula Ia.

Depending on their chemical structure, the compounds of formula I possess one or more isomeric centres and thus can be produced as optical isomers, or mixtures of these isomers. The mixtures of these isomers can be resolved, if desired, at appropriate stages by methods known to those skilled in the art to obtain the respective individual isomers.

Another object of the present invention is a pharmaceutical or veterinary composition containing as essential active ingredient at least one of the methylamine derivatives defined in formula I or a pharmaceutically acceptable acid addition salt thereof in association with an appropriate pharmaceutical carrier or excipient therefor.

A further object of the invention is to provide a process for preparing pharmaceutical or veterinary compositions whereby at least one methylamine derivative of formula I or a pharmaceutically acceptable acid addition salt thereof is placed in association with an appropriate pharmaceutical carrier or excipient. As will be described in greater detail further on, it has been found that the methylamine derivatives of formula I and their pharmaceutically acceptable acid addition salts possess pharmacological properties likely to render them particularly useful in the treatment of Parkinson's disease and for correcting extra-pyramidal disturbances provoked by neuroleptics.

In consequence, another object of the invention is to provide a method of treating Parkinson's disease and of correcting extra-pyramidal disturbances provoked by neuroleptics, which method comprises the administration at an effective dose to the patient so affected of at least one compound of formula I or a pharmaceutically acceptable acid addition salt thereof.

Daily dosage will preferably be between 10 and 60 mg of active principle for a human being weighing 60 kg.

Amongst the compounds of formula I, a certain number are believed to be novel.

The invention relates, in consequence, to the new derivatives of methylamine defined below, all of which are included in formula I:

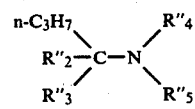

and the pharmaceutically acceptable acid addition salts thereof wherein $R''_2$ represents ethyl, n-propyl, isopropyl, isobutyl or allyl, $R''_3$ represents ethyl, n-propyl, isopropyl, n-butyl, isobutyl or tert-butyl, $R''_4$ represents hydrogen, propargyl or 2-hydroxyethyl, $R''_5$ represents hydrogen, methyl, propargyl, 2-hydroxyethyl or 3-hydroxy-n-propyl or $R''_4$ and $R''_5$, when they are taken together, represent methylene, ethylene, trimethylene, ethylidene or the radical —CH₂—CH₂—O—CH- 2—$CH_2$— with the proviso that the methylamine derivatives of formula Ib are other than 1,1-di-n-propyl-n-butylamine in base form or the hydrochloride thereof.

A class of preferred new derivatives of formula Ib can be represented by the following general formula:

Ic and the pharmaceutically acceptable acid addition salts thereof wherein $R''_5$ represents methyl or propargyl and $R''_2$ is such that when $R''_5$ represents methyl, $R''_2$ represents n-propyl, isopropyl, isobutyl or allyl and when $R''_5$ represents propargyl, $R''_2$ is n-propyl.

General formula Ic represents, therefore the following methylamine derivatives:

N-Methyl-1,1-di-n-propyl-n-butylamine
N-Methyl-1-n-propyl-1-isopropyl-n-butylamine
N-Methyl-1-n-propyl-1-isobutyl-n-butylamine
N-Methyl-1-n-propyl-1-allyl-n-butylamine
N-Propargyl-1,1-di-n-propyl-n-butylamine as well as their pharmaceutically acceptable acid addition salts, preferably the hydrochloride or the acid fumarate.

There are, however, a certain number of the compounds of the invention which are already known. In this connection may be cited, for example:

1,1-Di-(2-propen-1-yl)-3-buten-1-ylamine or triallyl-methylamine described in the J. Amer. Chem. Soc., 65, 87 (1943)

1,1,3,3-Tetramethyl-n-butylamine published in the J. Amer. Chem. Soc., 70, 4048 (1948)

1-Methyl-1-ethyl-2-pentyn-1-ylamine
1-Methyl-1-ethyl-2-heptyn-1-ylamine
1-Methyl-1-ethyl-n-pentylamine
1-Methyl-1-ethyl-n-propylamine
1-Methyl-1-ethyl-2-propen-1-ylamine all of which are described in the J. Amer. Chem. Soc., 75, 4297 (1953)

1,1-Diethyl-2-propyn-1-ylamine
1,1-Dimethyl-2-propyn-1-ylamine
1,1-Diethyl-n-propylamine which are already on the market.

However, as far as is known, no therapeutic activity has ever been attributed to these known compounds.

Similarly, tri-n-propylmethylamine or 1,1-di-n-propyl-n-butylamine and tri-n-butylmethylamine or 1,1-di-n-butyl-n-pentylamine have been described by SPERBER et al. in the J. Amer. Chem. Soc., 71, 3352 (1949), where they are presented as being "less spasmolytic and more toxic than the corresponding trialkylethylamines". Here it is more a question of a musculotropic antispasmodic activity as pointed out in the reference in question.

Independently of the fact that the information supplied in this publication concerning these two compounds of formula I is completely lacking in precision, there is nothing in this text which could even remotely suggest the activities which, in the light of the present invention, can be attributed to the compounds of formula I in general and to tri-n-propyl- and tri-n-butyl-methylamines in particular.

The publication relating to the spasmolytic activity thus attributed to the two methylamine derivatives in question does not, in fact, give any details as regards degree of activity nor does it make any allusion to the method by which the spasmolytic activity was demonstrated. Furthermore, no toxicity data are given. The pharmacological information published by SPERBER et al. is therefore too vague to enable anyone to deduce that tri-n-propyl- and tri-n-butyl methylamines have sufficient spasmolytic activity at non-toxic doses to make them likely to be of use as therapeutic agents.

In the course of the pharmacological trials carried out with the compounds of formula I, the spasmolytic activity of tri-n-propylmethylamine or 1,1-di-n-propyl-n-butylamine was investigated "in vitro". In full agreement with the findings of SPERBER et al. it was observed that the spasmolytic activity of this compound is very weak, in fact practically non-existent since it is 20,000 to 25,000 times weaker than that of atropine. From this it may be reasonably deduced that the spasmolytic activity of tri-n-propylmethylamine should be exerted "in vivo" at doses which are extremely toxic.

Pharmacological trials carried out "in vivo" have, in fact, shown that at the doses at which tri-n-propylmethylamine can be used against Parkinson's disease and as an agent for correcting the extrapyramidal disturbances provoked by neuroleptics, i.e. at doses well below the toxic dose, the spasmolytic activity of this compound is non-existent.

Other compounds included within the scope of formula I hereabove are covered by U.S. Pat. Nos. 2,230,752; 2,606,923; 2,766,285 and 3,067,101 and by Canadian Pat. No. 522,710. Similarly, methylamine derivatives, which are covered by the present invention have already been disclosed in Collection Czechoslov. Chem. Commun. Vol. 35, pp 2810–2814 (1970), in J. Pharmacol. Exptl. Therap. 98, 300–4 (1950) and in Arch. Immunol. Therap. Exptl. 10, (4), 905–924 (1962).

These compounds are presented in these patents and publications as possessing pharmacological activities including antispasmodic, antitubercular, broncho-dilating, hypotensive and ganglionic blocking actions.

However, there is nothing in these texts which could suggest even remotely that the methylamine derivatives of the present invention could act on the central nervous system. For example, an antispasmodic compound will not be automatically endowed with a central action capable of rendering it useful in Parkinsonism and there is no correlation between an antispasmodic action on smooth muscle and an action on the central nervous system. This fact is reported by Goodman & Gilman in "The Pharmacological Basis of Therapeutics" (The Macmillan Company) on pages 524 and 525.

The compounds of formula I in which $R_1$ and $R_3$ each represent an atom of hydrogen or an alkyl, alkenyl or alkynyl radical and $R_2$ represents an alkyl radical, an alkenyl radical other than $CH=CH-R_6$ or an alkynyl radical other than $C\equiv C-R_6$ may be prepared by treating, in an appropriate medium, with a strong acid such as, for example, hydrochloric or sulphuric acid, an isocyanate or a N-formyl amine of the general formula:

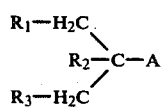

II wherein $R_1$, $R_2$ and $R_3$ have the above meanings and A represents the group $N=C=O$ or $NH-CO-H$, to form the corresponding acid addition salt of the required compound of formula I which, if desired, may be reacted with a base such as, for example, sodium hydroxide to obtain the compound of formula I in the form of its free base which may then be reacted with an organic or inorganic acid to give a different pharmaceutically acceptable acid addition salt.

The treatment of the compound of formula II with the acid may be carried out by utilizing the reagents involved at a temperature between 15° C. and 100° C., and preferably between 50° C. and 90° C.

The compounds of formula I in which $R_1$ and $R_3$ each represent an alkyl radical containing from 1 to 3 atoms of carbon or an alkenyl or alkynyl radical containing 2 or 3 atoms of carbon and $R_2$ represents the radical $CH_2$-$R_7$ in which $R_7$ represents an alkyl radical containing from 1 to 3 carbon atoms or an alkenyl or alkynyl radical having 2 or 3 atoms of carbon, $R_1$, $R_3$ and $R_7$ being identical, can also be prepared by heating, in an anhydrous ether, such as for example ethyl ether, a nitrile of the general formula:

$$R_7-CH_2-CN \qquad III$$

in which $R_7$ has the above meaning with an organomagnesium derivative of the general formula:

$$R_7-CH_2MgX \qquad IV$$

in which $R_7$ has the same meaning as above and X represents an atom of chlorine, bromine or iodine, and hydrolyzing the complex thus formed to obtain the desired compound of formula I which may then be reacted with an organic or inorganic acid to provide a pharmaceutically acceptable acid addition salt of the said compound.

As hydrolyzing agent, use may be made, for example, of a saturated solution of ammonium chloride.

The compounds of formula I in which $R_1$ and $R_3$ each represent an atom of hydrogen or an alkyl radical and $R_2$ represents an alkynyl radical of the formula $C\equiv C-R_6$ in which $R_6$ represents hydrogen, i.e. an ethynyl radical, may be prepared in liquid ammonia by reacting sodium amide and a halide of the general formula:

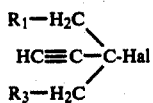

in which $R_1$ and $R_3$ have the meaning given above and Hal represents an atom of chlorine or bromine to give the desired compound of formula I which may then be reacted with an organic or inorganic acid to provide a pharmaceutically acceptable acid addition salt of the said compound.

The compounds of formula I in which $R_1$ and $R_3$ each represent an atom of hydrogen or an alkyl radical and $R_2$ represents an alkynyl radical of the formula $C\equiv C-R_6$ in which $R_6$ represents an alkyl radical containing from 1 to 5 atoms of carbon may be prepared by reacting a metallic derivative of the general formula:

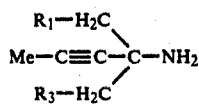

in which Me represents an atom of alkali metal such as, for example, sodium and $R_1$ and $R_3$ have the meaning given above with a halide of the formula:

$$R_6-Hal \qquad VII$$

in which $R_6$ has the meaning given above and Hal has the same meaning as in formula V to obtain the required compound of formula I which may then be reacted with an organic or inorganic acid to provide a pharmaceutically acceptable acid addition salt of the said compound.

The compounds of formula I in which $R_1$ and $R_3$ each represent an atom of hydrogen or an alkyl radical and $R_2$ represents an alkenyl radical of the formula $CH=CH-R_6$ in which $R_6$ has the same meaning as in the definition of formula I may be prepared by hydrogenating in an appropriate solvent such as, for example, heptane, and in the presence of a Lindlar catalyst, an amine of the general formula:

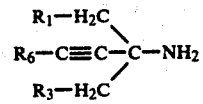

in which $R_1$, $R_3$ and $R_6$ have the meaning given above, to provide the required compound of formula I which may then be reacted with an organic or inorganic acid to obtain a pharmaceutically acceptable acid addition salt of the said compound.

The operation of hydrogenation is preferably carried out at a temperature between 30° C. and 60° C. and generally at about 50° C.

The compounds of formula II may be prepared in various ways, namely:

(a) when A represents the radical $N=C=O$: either by reacting an acetamide derivative of the general formula:

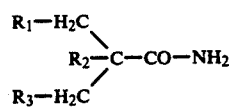

in which $R_1$, $R_2$ and $R_3$ have the same meaning as in formula II with chlorine or bromine in an alkaline medium such as, for example, in an aqueous solution of sodium or potassium hydroxide, or by reacting an acetic acid derivative of the general formula:

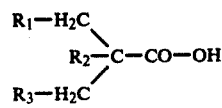

in which $R_1$, $R_2$ and $R_3$ have the same meaning as in the compounds of formula II above with a chlorinating agent such as, for example, thionyl or oxalyl chloride, to obtain the corresponding acyl chloride which is then treated with an alkali metal azide such as, for example, sodium azide, which provides the required compound of formula II, or following another process, by heating a compound of formula X directly with hydrogen azide in an acid medium, for example, sulphuric acid, to obtain the desired compound of formula II.

In this latter case, the isocyanate thus formed is immediately converted by hydrolysis to the corresponding amine of formula I.

(b) When A represents the radical NH—CO—H: by heating a tertiary alcohol of the general formula:

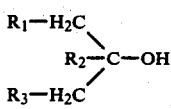    XI in which $R_1$, $R_2$ and $R_3$ have the same meaning as that given for the above compounds of formula II, with an alkaline cyanide such as, for example, sodium or potassium cyanide in the presence of an acid such as, for example, sulphuric acid.

The N-substituted compounds of formula I can also be prepared by means of different procedures in accordance with their chemical structure.

Thus, the compounds of formula I wherein $R_1$, $R_2$ and $R_3$ have the meaning given therein, $R_4$ represents hydrogen or a straight-or branched-chain alkyl, alkenyl or alkynyl radical containing from 1 to 5 carbon atoms and $R_5$ represents a straight- or branched-chain alkyl, alkenyl or alkynyl radical containing from 1 to 5 carbon atoms can be prepared by heating, in the presence of an alkaline agent, such as for example, sodium bicarbonate, an amine of the general formula:

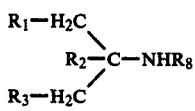    XII or an acid addition salt thereof, such as for example the hydrochloride, in which $R_1$, $R_2$ and $R_3$ have the same meaning as in formula I and $R_8$ represents hydrogen or an alkenyl, alkynyl or alkyl group containing from 1 to 5 carbon atoms, with an appropriate quantity of a halide of the general formula:

$R_9X$    XIII wherein $R_9$ represents a straight- or branched-chain alkyl, alkenyl or alkynyl radical having from 1 to 5 carbon atoms and X represents a chlorine, bromine or iodine atom, this reaction being undertaken either without any solvent or in the presence of a solvent, such as for example ethanol, to obtain the required compound of formula I which may then be reacted with an organic or inorganic acid to provide a pharmaceutically acceptable acid addition salt of the said compound.

In accordance with known chemical procedures and when it is desired to obtain a compound of formula I having two identical substituents on the nitrogen atom, the appropriate compound of formula XII i.e. a compound of formula XII wherein $R_1$, $R_2$ and $R_3$ have the desired meaning and $R_8$ represents hydrogen, is treated so that two molar equivalents of the halide of formula XIII react with one molar equivalent of the compound of formula XII.

Likewise, when it is desired to obtain a compound of formula I having a hydrogen atom on the nitrogen atom, the appropriate compound of formula XII i.e. a compound of formula XII wherein $R_1$, $R_2$ and $R_3$ have the desired meaning and $R_8$ represents hydrogen is treated so that one molar equivalent of the halide of formula XIII, reacts with one molar equivalent of the compound of formula XII.

It is well known that when a compound of formula I which is monosubstituted on the nitrogen atom is desired, there will be obtained a mixture containing, in addition to the desired monosubstituted compound, a certain proportion of the corresponding compound of formula I which is disubstituted on the nitrogen atom, even when the molar equivalents indicated above are employed.

Similarly, a certain amount of compound monosubstituted on the nitrogen atom will be formed when the corresponding compound disubstituted on the nitrogen atom is desired.

Such mixtures of mono- and di-substituted derivatives can be separated out by known techniques, for example by fractional distillation of the reaction mixture containing them or by fractional crystallization from their salts.

The compounds of formula I in which $R_1$, $R_2$ and $R_3$ have the meaning given therein, $R_4$ represents an ω-hydroxyalkyl radical having from 1 to 5 carbon atoms, i.e. a radical of the formula $-CH_2-(CH_2)_n-CH_2OH$ wherein n represents 0,1,2 or 3 and $R_5$ represents hydrogen, an ω-hydroxyalkyl radical such as defined hereabove or a straight- or branched-chain alkyl, alkenyl or alkynyl radical having from 1 to 5 carbon atoms may be obtained by treating, by means of an appropriate reducing agent, such as for example, lithium aluminium hydride, and in an inert and anhydrous medium, such as for example ethyl ether, an ω-halogenated ester of the general formula:

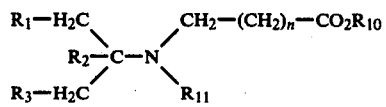    XIV wherein $R_1$, $R_2$ and $R_3$ have the same meaning as in formula I, $R_{10}$ represents a straight- or branched-chain alkyl radical having from 1 to 4 carbon atoms, n has the meaning given hereabove and $R_{11}$ represents hydrogen, a straight- or branched-chain alkyl, alkenyl or alkynyl radical having from 1 to 5 carbon atoms or a radical of the formula $CH_2-(CH_2)_n-CO_2R_{10}$ in which $R_{10}$ and n have the same meaning given hereabove, to obtain the desired compound of formula I which may then be reacted with an organic or inorganic acid to provide a pharmaceutically acceptable acid addition salt of the said compound.

The compounds of formula I wherein $R_1$, $R_2$ and $R_3$ have the meaning given therein and $R_4$ and $R_5$, when they are taken together, represent an alkylene radical having from 2 to 6 carbon atoms, i.e. a radical of the formula $-CH_2-(CH_2)_m-CH_2-$ in which m represents 0, 1, 2, 3 or 4 or the radical $-CH_2-CH_2-O-CH_2-CH_2-$, can be obtained in a solvent or in the absence of a solvent by reacting an appropriate cyclization agent with a methylamine derivative of the general formula:

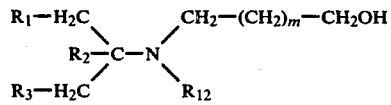    XV in which $R_1$, $R_2$ and $R_3$ have the same meaning as in formula I, m has the meaning given hereabove and $R_{12}$ represents hydrogen or the radical $CH_2—CH_2OH$, with the proviso that when $R_{12}$ represents $CH_2—CH_2OH$, m represents O, which provides the desired compound of formula I which may then be reacted with an organic or inorganic acid to provide a pharmaceutically acceptable acid addition salt of the said compound.

When $R_{12}$ represents hydrogen, the compound of formula XV hereabove can also be used in the form of an addition salt such as for example the hydrochloride.

The cyclization operation which is involved in the aforesaid process can be effected:

(a) in the absence of a solvent or in the presence of a solvent, such as for example benzene, by means of a suitable agent, such as for example chlorosulphonic acid, (b) in a solvent such as for example acetonitrile or benzene, by means of a suitable agent such as for example triphenylphosphine bromide and in the presence of an organic base, such as for example triethylamine, (c) in a solvent such as for example benzene, by means of a suitable agent, such as for example phosphoric anhydride.

The cyclization agent will be chosen in accordance with the structure of the compound of formula XV. For example, chlorosulphonic acid or triphenylphosphine bromide can be used when in the compound of formula XV $R_1$, $R_2$ and $R_3$ each represent an alkyl radical, $R_{12}$ represents the radical $CH_2—CH_2OH$ and m is 0.

The compounds of formula I wherein $R_1$, $R_2$ and $R_3$ have the meaning given therein and $R_4$ and $R_5$, when they are taken together represent an alkylidene radical having from 1 to 5 carbon atoms can be obtained by condensing a methylamine derivative of the general formula:

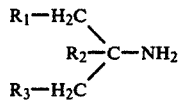

XVI wherein $R_1$, $R_2$ and $R_3$ have the same meaning as in formula I, with an aldehyde or a ketone of the general formula:

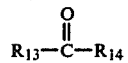

XVII wherein $R_{13}$ represents a straight- or branched-chain alkyl, alkenyl or alkynyl radical, having from 1 to 5 carbon atoms and $R_{14}$ represents hydrogen or a straight- or branched-chain alkyl, alkenyl or alkynyl radical having from 1 to 5 carbon atoms, the operation of condensation being carried out either in the absence of a solvent or in the presence of a solvent, such as for example benzene, to provide the desired compound of formula I which may then be reacted, if desired, with an organic or inorganic acid to provide a pharmaceutically acceptable acid addition salt.

A certain number of N-substituted methylamine derivatives of formula I can also be obtained in accordance with other methods than those already desired herein.

The different procedures set out hereunder for the preparation of some compounds of formula I are also included in the present invention, in addition to the general methods described above for the preparation of the whole of the methylamine derivatives covered by the invention.

For example, the compounds of formula I wherein $R_1$ and $R_3$ have the meaning cited therein and $R_2$ represents an alkyl radical, an alkenyl radical other than $CH=CH—R_6$ or an alkynyl radical other than $C\equiv C—R_6$, $R_4$ represents hydrogen and $R_5$ represents methyl, can also be prepared by reducing, with lithium aluminium hydride, an isocyanate of general formula II in which $R_1$, $R_2$ and $R_3$ have the above meaning and A represents $N=C=O$ to provide the required methylamine derivative of formula I, which can further be treated with an organic or inorganic acid to give a pharmaceutically acceptable acid addition salt.

The reduction in question can be effected in an inert and anhydrous medium such as for example ethyl ether.

Likewise, the compounds of formula I in which $R_1$, $R_2$ and $R_3$ have the meaning cited therein, $R_4$ represents hydrogen and $R_5$ represents an alkyl, alkenyl or alkynyl radical having from 1 to 5 carbon atoms can be prepared starting with a compound of the general formula:

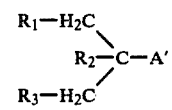

XVIII wherein $R_1$, $R_2$ and $R_3$ have the meaning given in formula I and A' represents H or $NH—CO—R_{15}$ or $N=CH—R_{15}$ in which $R_{15}$ represents an alkyl, alkenyl or alkynyl radical having from 1 to 4 carbon atoms and reducing this compound:

(a) in an appropriate anhydrous medium, such as for example ethyl or butyl ether, with lithium aluminium hydride in the case where A' represents $NH—CO—R_{15}$ (b) in a solvent such as for example methanol, with sodium borohydride in the case where A' represents $N=CH—R_{15}$, to provide the required compound of formula I which can then be treated, if desired, with an organic or inorganic acid to obtain a pharmaceutically acceptable acid addition salt of this compound.

The compounds of formula I wherein $R_1$, $R_2$ and $R_3$ have the meaning cited therein, $R_4$ represents a straight- or branched-chain alkyl radical having from 1 to 6 carbon atoms and $R_5$ represents methyl can also be obtained by heating a methylamine derivative of the general formula:

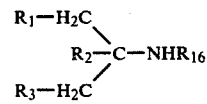

XIX or an acid addition salt thereof, for example the hydrochloride, wherein $R_1$, $R_2$ and $R_3$ have the same meaning as in formula I and $R_{16}$ represents hydrogen or a straight- or branched-chain alkyl radical having from 1 to 6 carbon atoms, in the presence of formic aldehyde and formic acid to give the desired compound of formula I which can then be reacted with an organic or inorganic acid to provide a pharmaceutically acceptable acid addition salt of this compound.

On the other hand, the compounds of formula I wherein $R_1$, $R_2$ and $R_3$ have the meaning cited therein, $R_4$ represents hydrogen and $R_5$ represents 2-hydroxyethyl can be obtained by reacting ethylene oxide with a methylamine derivative of general formula XVI, in the presence of an appropriate catalyst, such as for example boron trifluoride used preferably in the form of an etherate, to provide the desired compound of formula I which can then be treated with an organic or inorganic acid to obtain an acid addition salt of this compound.

The reaction in question will be effected by heating the reagents, preferably at a temperature between 170° and 200° C.

The compounds of formula I wherein $R_1$, $R_2$ and $R_3$ have the meaning cited therein and $R_4$ and $R_5$, which are identical, each represent an ω-hydroxyalkyl radical can also be prepared by reacting under pressure a molar equivalent of a methylamine derivative of the general formula XVI with two molar equivalents of an alkylene oxide of the general formula:

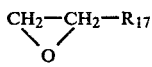 XX wherein $R_{17}$ represents hydrogen or an alkyl radical having from 1 to 3 carbon atoms, this reaction being undertaken in the presence of a strong acid, such as for example hydrochloric acid, and in an inert medium, such as for example methanol, to provide the desired compound of formula I which can further be reacted with an organic or inorganic acid to obtain a pharmaceutically acceptable acid addition salt of the said compound.

The reaction in question will be effected by heating the reagents, for example at a temperature between 40° and 80° C., preferably at 50° C. and under a pressure of 3 bars.

Likewise, the compounds of formula I wherein $R_1$, $R_2$ and $R_3$ have the meaning cited therein and $R_4$ and $R_5$, when they are taken together, represent the radical —$CH_2$—$CH_2$—O—$CH_2$—$CH_2$— can be prepared following other procedures than those mentioned hereabove.

Thus, the compounds in question of formula I can also be obtained by heating a methylamine derivative of formula XVI or an acid addition salt thereof, for example the hydrochloride, with di-(2-chloroethyl)oxide in the presence of an alkaline agent, such as for example sodium carbonate, to provide the desired compound of formula I which can further be reacted with an organic or inorganic acid to obtain a pharmaceutically acceptable acid addition salt of this compound.

Furthermore, the compounds of formula I in which $R_1$ and $R_3$ each represent hydrogen or a straight- or branched-chain alkyl radical having from 1 to 6 carbon atoms, $R_2$ represents a straight- or branched-chain alkyl, alkenyl or alkynyl radical having from 2 to 7 carbon atoms and $R_4$ and $R_5$, when they are taken together, represent the radical —$CH_2$—$CH_2$—O—$CH_2$—$CH_2$— can also be obtained by reacting, in an anhydrous ether, such as for example ethyl ether, a morpholine derivative of the general formula:

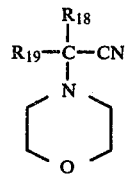 XXI wherein $R_{18}$ and $R_{19}$, which can be the same or different, each represent a straight- or branched-chain alkyl radical having from 1 to 7 carbon atoms with an organo-magnesium derivative of the general formula:

$R_2MgBr$      XXII in which $R_2$ has the same meaning as in formula I and further hydrolyzing the complex so formed to provide the desired compound of formula I which can then be reacted with an organic or inorganic acid to obtain a pharmaceutically acceptable acid addition salt of the said compound.

The compounds of formula IX can be obtained by reacting anhydrous ammonia with the corresponding acids of formula X or preferably with the halides of these acids. The acids can be prepared from the alcohols of formula XI and formic acid in a sulphuric acid medium.

The compounds of formula XI are either known compounds or can be prepared in accordance with known procedures such as, for example, by reacting an organolithium compound with an appropriate ketone in an anhydrous ether medium such as, for example tetrahydrofuran.

The compounds of formula V are either known products or can be prepared by the method described in the J. Org. Chem. 1961, 26, 725, i.e. by treating a 1,1-dialkyl-1-ethynyl-carbinol with cuprous chloride and hydrochloric acid in the presence of copper-bronze powder and calcium chloride. The 1,1-dialkyl-1-ethynyl-carbinols mentioned above are either known products, having been described in the Annales de Chimie, 1924, 10 (I), p 366, or can be prepared by known procedures described, for example, in Organic Syntheses Collective, Vol. III, p 416. The products of formula VI may be prepared in liquid ammonia through the action of an alkali metal such as, for example, sodium, on the corresponding 1,1-dialkyl-1-ethynyl-methylamine which is, in fact, a compound covered by formula I. The compounds of formula VIII are also included within the scope of formula I.

Amongst the compounds of formula XII those wherein $R_8$ represents hydrogen are in fact compounds represented by formula XVI hereabove. These compounds are all included within the scope of formula I. Likewise, the other compounds of formula XII, namely those wherein $R_8$ represents a straight- or branched-chain alkyl, alkenyl or alkynyl radical having from 1 to 5 carbon atoms are also compounds of formula I hereabove.

The compounds of formula XIV can be obtained by heating, in an appropriate medium, such as for example ethanol, and in the presence of an alkaline agent, such as for example sodium bicarbonate, a methylamine derivative of formula XII hereabove with an appropriate quantity of a halogenated compound of the general formula:

Hal—CH$_2$—(CH$_2$)$_n$—CO$_2$R$_{10}$      XXIII in which n and R$_{10}$ have the same meaning as in formula XIV and Hal represents an atom of chlorine, bromine, or iodine which gives the desired compound of formula XIV.

Furthermore, the compounds of formula XIV in which R$_{11}$ represents hydrogen, n represents 1 and R$_{10}$ has the same meaning as cited therein can also be prepared by heating in an inert medium, such as for example methanol, a methylamine derivative of general formula XVI with an acrylic acid ester of formula CH$_2$=CH—CO$_2$R$_{10}$ wherein R$_{10}$ has the same meaning as in formula XIV to obtain the desired compound.

The compounds of formulae XV and XIX are in fact compounds included within the scope of general formula I. With respect to the compounds of formula XVIII, those wherein A' represents N=CH—R$_{15}$ are covered by general formula I. Those wherein A' represents NH—CO—R$_{15}$ can be prepared either in the absence of a solvent or in a solvent, such as for example benzene, and in the presence of an acid acceptor, such as for example pyridine or 2,6-dimethyl-pyridine, by reacting a methylamine derivative of formula XVI with a halide or an anhydride of the general formula:

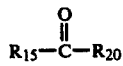

XXIV in which R$_{15}$ has the same meaning as in formula XVIII and R$_{20}$ represents an atom of chlorine, bromine or a radical O—CO—R$_{15}$ wherein R$_{15}$ has the same meaning as in formula XVIII, to provide the required compound.

The nitriles of formula XXI can be obtained by reacting potassium cyanide with a mixture of morpholine hydrochloride and a ketone of the general formula:

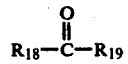

XXV in which R$_{18}$ and R$_{19}$ have the same meaning as in formula XXI, the reaction being carried out in an appropriate medium, such as for example methanol.

It has been discovered that the methylamine derivatives of formula I possess valuable pharmacological properties which are likely to render them useful in human and veterinary therapy.

In particular, it has been found that the compounds of the invention present central noradrenergic and central dopaminergic properties. These latter properties manifest themselves by an inhibitory action on reserpine-induced and neuroleptic-induced catatonia and catalepsy.

Pharmacological trials performed with the compounds of the invention have shown that tri-n-propyl-methylamine hydrochloride or 1,1-di-n-propyl-n-butylamine hydrochloride possesses a marked degree of activity. However, it was surprisingly and quite unexpectedly observed that 1,1-di-n-propyl-n-butylamine acid fumarate presents a degree of activity which is markedly greater than that of the corresponding hydrochloride. It was, in fact, observed that 1,1-di-n-propyl-n-butylamine acid fumarate is from 20 to 40 percent more active than the corresponding hydrochloride in tests involving reserpine-induced and neuroleptic-induced catatonia.

Furthermore, at doses which completely suppress neuroleptic-induced catatonia and catalepsy, it was observed that the compounds of the invention do not influence the anti-amphetamine effects of the neuroleptics in the rat and their anti-apomorphine effects in the dog. Furthermore, the compounds of the invention have no emetic action in the dog at any doses and are not cholinolytic agents.

These pharmacological properties taken as a whole are likely to render the compounds of formula I useful in treating Parkison's disease as well as for correcting extra-pyramidal disturbances provoked by neuroleptics.

Parkinson's disease is a chronic and progressive affection characterized in particular by a dopamine deficiency of the thalamus and the caudate and lenticular nuclei, with akinesia, rigidity and tremor as visible symptoms.

Many active drugs have already been proposed for combating Parkinson's syndrome. Most of these products are central anticholinergic agents with peripheral anti-cholinergic effects. These compounds are of natural origin, such as for example atropine, or are obtained synthetically, as for example diethazine, benztropine or trihexyphenidyl. However, these drugs may present undesirable side-effects, due in most cases to their peripheral anti-cholinergic properties, such side-effects taking the form, for example, of dryness of the mouth, difficulty in optical accommodation, tachycardia, constipation and retention of urine. These products will thus be contraindicated in cases of glaucoma and hypertrophy of the prostate.

L-Dopa or levodopa, a precursor of dopamine, has also been proposed in parkinsonism. However, in view of its partial destruction in the digestive system, L-dopa must be administered at very high doses, which very often induce indesirable side-effects. The most serious of these side-effects are cardiovascular in nature and in particular take the form of disturbances of cardiac rhythm and orthostatic hypotension. Patients treated with L-dopa must, therefore, not present contraindications on the cardiac plane.

Recently, amantadine i.e. 1-amino-adamantane has been proposed for antiparkinsonian therapy. This product, which stimulates the liberation of dopamine is very active but produces several undesirable side-effects and also decreases in activity after a certain length of time.

For this reason, it is very difficult for the doctor to select amongst the various antiparkinsonian drugs, that which will be effective for the case under treatment. Each patient must be considered as an individual case. All the known methods of treating Parkinson's disease are symptomatic and, in spite of the medication used, the disease continues to progress. The treatment of parkinsonism requires the successive use of one or more therapeutic substances and it is often necessary to institute therapeutic cycles. Frequently, two antiparkinsonian agents must be simultaneously administered, the first being considered as the basic drug and the second as an auxiliary or additional drug. Furthermore, since treatment is of long duration the alternating use of different products is necessary.

The search for new antiparkinsonian agents is therefore of primary importance. From this point of view, the compounds of formula I will constitute valuable additions to antiparkinsonian therapy, since at present there is no ideal agent for the treatment of this disease as explained in detail hereabove.

The compounds of the invention will consequently constitute valuable additions to the therapeutic arsenal at the disposal of the doctor and will provide useful replacement medication for any drug which has become ineffective for any reason such as a change in the state of the patient or habituation.

Although the pharmacological spectrum of the compounds of the invention is very similar to that of amantadine, pharmacological trials performed with the compounds of formula I have revealed marked differences in comparison with amantadine. For example, when comparing the doses of the compounds of the invention and of amantadine which have a certain degree of activity, it has been observed that the active dose in question is always proportionally farther from the toxic dose in the case of the compounds of the invention than in the case of amantadine. In other words, the safety margin offered by the compounds of the invention is superior to that of amantadine. Other differences which are particularly evident have been observed with the preferred compound of the invention, namely: tri-n-propylmethylamine or 1,1-di-n-propyl-n-butylamine in basic form or in the form of a pharmaceutically acceptable acid addition salt such as the hydrochloride or the acid fumarate.

For example, on the cardiovascular plane, it has been observed that the preferred compound of the invention does not cause any undesirable effect on the electrocardiogram whereas a dose of 5 mg/kg of amantadine injected into the dog provokes cardiac arrhythmia due to ventricular extrasystoles. It has also been found that the preferred compound of the invention does not potentiate the peripheral effects of norepinephrin and is not a ganglioplegic agent while tests performed with amantadine have demonstrated that this compound potentiates the peripheral adrenergic effects and furthermore exerts a ganglioplegic action.

The preferred compound of the invention which does not present these undesirable side-effects observed with amantadine will not therefor induce cardiac disturbances or disorders of arterial pressure.

As mentioned above, certain types of antiparkinsonian agents such as diethazine, benztropine etc. . . . frequently provoke undesirable side-effects of an anticholinergic nature (dryness of the mouth, difficulty in optical accomodation etc. . . .)

The preferred compound of the invention being devoid of anticholinergic activity does not present these disadvantages.

Similarly, the preferred compound of the invention as it is devoid of emetic properties and of undesirable side-effects on the electrocardiogram, will not provoke vomiting or cardiac arrhythmia which are two frequent side-effects of L-dopa.

In addition, pharmacological tests have shown that the new methylamine derivatives of the invention have a weak tremor-inducing action. This tremor-inducing action was even found to be less potent than that of 1,1-di-n-propyl-n-butylamine.

It is desirable that the tremor-inducing action in question be as weak as possible since tremors are the first sign of a motor stimulation which can be considered as an undesirable side-effect.

Such a motor stimulation frequently provokes mental and physical fatigue. In persons suffering from depression a phase of intensified mental depression can therefore occur which must, of course, be avoided.

A motor stimulation is also contra-indicated in epileptic patients since it can give rise to seizures.

Moreover, pharmacological tests have shown that N-methyl-1,1-di-n-propyl-n-butylamine is practically devoid of inhibitory effects on the monoamine oxidase which frequently provokes undesirable side effects such as tachycardia, hypotension and paroxystic hypertension.

Pharmacological trials have been performed with a view to determining the various properties of the compounds of the invention which, taken together, are capable of rendering the said compounds useful in the treatment of Parkinson's disease and for the correction of extrapyramidal disturbances induced by neuroleptics.

I. INHIBITION OF RESERPINE-INDUCED AND NEUROLEPTIC-INDUCED CATATONIA (DOPAMINERGIC PROPERTIES)

1. Inhibition of reserpine-induced catatonia

After sufficient doses of reserpine have been administered to the rat, a series of symptoms occur, more particularly ptosis, catatonia and a drop in central temperature. These symptoms are caused by the depletion of the intragranular reserve pool of biogenetic amines at the synaptic terminals.

The antidepressants of the tricyclic type as well as the inhibitors of monoamine oxidase (I.M.A.O.) antagonize more particularly the appearance of ptosis and the drop in central temperature. On catatonia, the action of such compounds is not non existent but is considerably less marked.

As against this, the synthetic antiparkinsonian agents principally influence catatonia while their activity on ptosis and hypothermia is non existent or weaker.

An oral dose of the compound to be studied in aqueous solution was administered to batches of 10 male rats of the OFA strain weighing about 150 to 200 g. Thirty minutes later a dose of 5 mg/kg of reserpine was given by intraperitoneal route. Three hours after the injection of reserpine, the animals were suspended by the four paws to a horizontally stretched wire fixed at 15 cm from the ground. The catatonia animals were those which maintained the position so given for at least 30 seconds. Each animal which maintained the position so given received the score of 1 and those which did not maintain the said position were given the score of 0. The maximum score was therefore 10 per batch. An identical trial was undertaken with control animals which received reserpine but none of the compounds being studied.

The following compounds of formula I were tested in comparison with amantadine in accordance with the process indicated hereabove. These compounds were preferably studied in the form of a pharmaceutically acceptable acid addition salt such as the hydrochloride or the fumarate.

1,1-Di-n-propyl-n-butylamine (Compound 1)
1-Ethyl-1-n-propyl-n-butylamine (Compound 2)
1-Ethyl-1-isobutyl-n-butylamine (Compound 3)
1-Ethyl-1-n-propyl-n-pentylamine (Compound 4)
1-n-Propyl-1-isobutyl-n-butylamine (Compound 5)
1,3-Dimethyl-1-n-propyl-n-pentylamine (Compound 6)
1,3-Dimethyl-1-ethyl-n-hexylamine (Compound 7)
1-Methyl-1-isobutyl-n-pentylamine (Compound 8)
1-Methyl-1-n-propyl-n-hexylamine (Compound 9)
1,1-Dimethyl-n-octylamine (Compound 10)

1,1-Di-(2-propen-1-yl)-3-buten-1-ylamine (Compound 11)
1,1-Di-n-butyl-n-pentylamine (Compound 12)
1,1,3-Trimethyl-n-heptylamine (Compound 13)
1,1-Diethyl-n-butylamine (Compound 14)
1,1-Diethyl-n-propylamine (Compound 15)
1,1-Dimethyl-n-propylamine (Compound 16)
1,1-Dimethyl-3-ethyl-n-hexylamine (Compound 17)
1,1-Diisobutyl-n-butylamine (Compound 18)
1-n-Propyl-1-isobutyl-n-butylamine (Compound 19)
1-n-Propyl-1-tert-butyl-n-butylamine (Compound 20)
1,1-Di-n-propyl-2-propyn-1-ylamine (Compound 21)
1,1-Diethyl-2-pentyn-1-ylamine (Compound 22)
1,1-Diethyl-2-penten-1-ylamine (Compound 23)
1,1-Di-n-propyl-2-pentyn-1-ylamine (Compound 24)
1,1-Di-n-propyl-2-penten-1-ylamine (Compound 25)
1,1-Di-n-propyl-3-butyn-1-ylamine (Compound 26)
N-Methyl-1,1-di-n-propyl-n-butylamine (Compound 27)
N,N-Dimethyl-1,1-di-n-propyl-n-butylamine (Compound 28)
N,N-Trimethylene-1,1-di-n-propyl-n-butylamine (Compound 29)
N-Methyl-1-n-propyl-1-isopropyl-n-butylamine (Compound 30)
N-Methyl-1-n-propyl-1-isobutyl-n-butylamine (Compound 31)
N-Methyl-1-n-propyl-1-allyl-n-butylamine (Compound 32)
N-Ethyl-1,1-di-n-propyl-n-butylamine (Compound 33)
N-Isopropyl-1,1-di-n-propyl-n-butylamine (Compound 34)
N-Allyl-1,1-di-n-propyl-n-butylamine (Compound 35)
N-Propargyl-1,1-di-n-propyl-n-butylamine (Compound 36)
N,N-Dimethyl-1-n-propyl-1-isobutyl-n-butylamine (Compound 37)
N-Methyl-N-ethyl-1,1-di-n-propyl-n-butylamine (Compound 38)
N,N-Dipropargyl-1,1-di-n-propyl-n-butylamine (Compound 39)
N,N-Ethylene-1,1-di-n-propyl-n-butylamine (Compound 40)
N-Methylene-1,1-di-n-propyl-n-butylamine (Compound 41)
N-Ethylidene-1,1-di-n-propyl-n-butylamine (Compound 42)
N-(2-Hydroxyethyl)-1,1-di-n-propyl-n-butylamine (Compound 43)
N,N-bis-(2-Hydroxyethyl)-1,1-di-n-propyl-n-butylamine (Compound 44)
N-(3-Hydroxy-n-propyl)-1,1-di-n-propyl-n-butylamine (Compound 45)
N,N-(3-Oxapentamethylene)-1,1-di-n-propyl-n-butylamine (Compound 46)

The results obtained with the compounds of formula I listed hereabove as well as with amantadine are given in Table I hereunder. These results are expressed in the following manner:

0: represents 0% inhibition of catatonia in comparison with the controls (namely a score of 10 per studied batch).
1: represents 20 to 30% inhibition of catatonia in comparison with the controls (namely a score of 7 to 8 per studied batch).
2: represents 50% inhibition of catatonia in comparison with the controls (namely a score of 5 per studied batch)
3: represents 70 to 80% inhibition of catatonia in comparison with the controls (namely a score of 2 or 3 per studied batch).
4: represents 100% inhibition of catatonia in comparison with the controls (namely a score of 0 per studied batch).

Table I

| Compound | Dose administered in mg/kg | Inhibition of reserpine-induced catatonia |
| --- | --- | --- |
| 1 | 5 | 4 |
| 2 | 5 | 1 |
| 3 | 20 | 3 |
| 4 | 20 | 3 |
| 5 | 20 | 2 |
| 6 | 20 | 1 |
| 7 | 20 | 1 |
| 8 | 20 | 1 |
| 9 | 20 | 1 |
| 10 | 20 | 1 |
| 11 | 20 | 1 |
| 12 | 20 | 1 |
| 13 | 25 | 1 |
| 14 | 50 | 3 |
| 15 | 50 | 1 |
| 16 | 50 | 1 |
| 17 | 11 | 1 |
| 18 | 12 | 2 |
| 19 | 6 | 3 |
| 20 | 6 | 2 |
| 21 | 30 | 2 |
| 22 | 60 | 1 |
| 23 | 60 | 1 |
| 24 | 20 | 1 |
| 25 | 6 | 3 |
| 26 | 30 | 1 |
| 27 | 6 | 4 |
| 28 | 6 | 4 |
| 29 | 6 | 4 |
| 30 | 6 | 4 |
| 31 | 6.5 | 3 |
| 32 | 5 | 2 |
| 33 | 6 | 2 |
| 34 | 6.5 | 2 |
| 35 | 6 | 2 |
| 36 | 6 | 1 |
| 37 | 6.5 | 3 |
| 38 | 6.5 | 2 |
| 39 | 15 | 2 |
| 40 | 6 | 2 |
| 41 | 5.5 | 4 |
| 42 | 6 | 4 |
| 43 | 13 | 3 |
| 44 | 15 | 1 |
| 45 | 14 | 2 |
| 46 | 8 | 1 |
| Amantadine | 100 | 4 |

These results show that Compound 1 which is the preferred compound of the invention is as active as amantadine but at a dose which is twenty times inferior to that of amantadine. Complementary trials have shown that at a dose of 13 mg/kg, Compound 34 causes inhibition of reserpine-induced catatonia equal to 4 while, at a dose as low as 3 mg/kg, the index of inhibition reserpine-induced catatonia of Compound 29 is equal to 3.

2. Inhibition of neuroleptic-induced catatonia

The blocking of dopaminergic receptors by neuroleptics in the extra-pyramidal system induces catatonia in the rat. Catatonia is differentiated from sedative properties by means of the test used hereabove for reserpine-induced catatonia. The same system of scoring was also employed in the present case.

An oral dose of the compound to be studied in aqueous solution was administered to batches of 10 male rats of the OFA strain weighing about 150 to 200 g. Thirty minutes later a dose of 12.5 mg/kg of prochlorperazine was given by intraperitoneal route.

Three hours after the injection of this latter compound, catatonia was measured. An identical trial was also carried out with control animals which received prochlorperazine but none of the compounds under study.

The results obtained with the above-listed compounds in comparison with amantadine are set out in the following Table II together with the results obtained with the compound hereunder: N-n-propyl-1,1-di-n-propyl-n-butylamine (Compound 47)

The scoring system used was that given hereabove for Table I.

Table II

| Compound | Dose administered in mg/kg | Inhibition of the neuroleptic-induced catatonia |
|---|---|---|
| 1 | 5 | 4 |
| 2 | 5 | 1 |
| 3 | 20 | 3 |
| 4 | 20 | 3 |
| 5 | 20 | 4 |
| 6 | 20 | 1 |
| 7 | 40 | 1 |
| 8 | 50 | 4 |
| 9 | 20 | 1 |
| 10 | 50 | 1 |
| 11 | 20 | 1 |
| 12 | 20 | 1 |
| 13 | 50 | 1 |
| 14 | 50 | 3 |
| 15 | 50 | 3 |
| 16 | 10 | 1 |
| 17 | 11 | 2 |
| 18 | 12 | 1 |
| 19 | 6 | 3 |
| 20 | 50 | 1 |
| 21 | 30 | 1 |
| 22 | 30 | 1 |
| 23 | 30 | 1 |
| 24 | 20 | 2 |
| 25 | 6 | 3 |
| 26 | 30 | 4 |
| 27 | 6 | 3 |
| 28 | 6 | 4 |
| 29 | 6 | 4 |
| 30 | 6 | 3 |
| 31 | 6.5 | 4 |
| 32 | 5 | 2 |
| 33 | 6 | 4 |
| 34 | 6.5 | 4 |
| 35 | 6 | 4 |
| 36 | 6 | 4 |
| 37 | 6.5 | 2 |
| 38 | 6.5 | 2 |
| 40 | 6 | 1 |
| 41 | 5.5 | 3 |
| 42 | 6 | 2 |
| 43 | 6.5 | 1 |
| 44 | 15 | 1 |
| 45 | 7 | 2 |
| 46 | 8 | 2 |
| 47 | 6.5 | 2 |
| Amantadine | 100 | 4 |

These results show that Compound 1 is also twenty times more active than amantadine in this test and that Compound 5 is five times more active than amantadine while Compound 8 is twice as active.

Furthermore Compound 1 at a dose as low as 1 mg/kg, provokes a 70% inhibition of the neuroleptic-induced catatonia.

Complementary tests have been shown that Compounds 28, 29 and 34 at a dose as low as 3 mg/kg have an index of inhibition of neuroleptic-induced catatonia equal to 2 while Compound 40 at the dose of 12 mg/kg has an index equal to 3.

The results mentioned in the above Tables I and II in connection with Compound 1 were obtained with 1,1-di-n-propyl-n-butylamine in the form of its hydrochloride. In the form of its acid fumarate, 1,1-di-n-propyl-n-butylamine is from 20 to 40 percent more active as previously indicated. For example, a score of 4 was obtained in the tests involving reserpine-induced and neuroleptic-induced catatonia as described hereabove with only 3 mg/kg of 1,1-di-n-propyl-n-butylamine acid fumarate.

II. Tremor-inducing action

The following test was performed with N-substituted methylamines in comparison with 1,1-di-n-propyl-n-butylamine. Batches of 10 rats were given 0.031 m mol/kg of the compound to be studied by oral route.

Thirty minutes after administration, note was taken of the number of animals presenting tremors and the following ratio was calculated:

$$\frac{\text{index of reserpine-induced catatonia}}{\text{number of animals presenting tremors}}$$

The index of reserpine-induced catatonia was expressed by figures from 0 to 4 such as previously described.

The following results were registered with compounds studied in the hydrochloride form:

| Compound | Index of reserpine-induced catatonia / Number of animals presenting tremors |
|---|---|
| 27 | 4/4 = 1 |
| 30 | 4/3 = 1.33 |
| 32 | 3/0 |
| 36 | 3/5 = 0.60 |
| 1 | 4/10 = 0.40 |

These results show that the ratio is always more advantageous with the N-substituted compounds than with the comparison compound which is non N-substituted.

III. Acute toxicity

In the acute toxicity test the $LD_{50}$ was determined on mice by oral route using the method of LICHFIELD and WILCOXON (J. Pharmacol. 1938, 2, 192–216). The compounds were administered in aqueous solution and the period of observation was 10 days after administration of the compound under study.

The following results were recorded in comparison with amantadine:

| Compound | $LD_{50}$ (in mg/kg) |
|---|---|
| 1 | 100 |
| 2 | 150 |
| 6 | >500 |
| 9 | 1750 |
| 12 | 500 |
| 27 | 100 |
| 29 | 65 |
| 30 | >150 |
| 32 | 170 |
| 33 | 100 |
| 35 | 130 |
| 36 | >150 |
| 37 | 110 |
| 38 | >120 |
| 39 | >150 |

| Compound | LD$_{50}$ (in mg/kg) |
|---|---|
| 40 | >150 |
| 41 | >150 |
| 42 | 120 |
| 43 | 150 |
| 45 | 140 |
| 46 | 250 |
| Amantadine | 1050 |

These results show that compounds of the invention are in general more toxic than amantadine. However, when a comparison is made between the LD$_{50}$ given hereabove and the effective dose to obtain inhibition of reserpine-induced or neuroleptic-induced catatonia, it is seen that such comparisons are always more favourable to the compounds of the invention than to amantadine. The index (LD$_{50}$/ED$_{20-30}$) was determined. In this index, ED$_{20-30}$ represents the effective dose to obtain 20 to 30% inhibition of the catatonia, this value being represented by the FIG. 1 in Tables I and II.

The following results are registered:

| Compound | Index |
|---|---|
| 2 | 30 |
| 6 | >25 |
| 9 | 87 |
| 12 | 25 |
| 36 | >25 |
| 40 | >25 |
| 43 | 23 |
| 46 | 31 |

The corresponding index for amantadine is (1050/50)=21, which shows that the compounds of the invention present greater advantages than amantadine.

Similarly, an index (LD$_{50}$/ED$_{100}$) was determined, ED$_{100}$ representing the effective dose to obtain 100% inhibition of the catatonia.

This latter value is represented in Tables I and II by the FIG. 4.

The following results were recorded:

| Compound | Index |
|---|---|
| 1 | 20 |
| 27 | 16.5 |
| 30 | >25 |
| 33 | 16.5 |
| 34 | 21.6 |
| 35 | 21 |
| 29 | 10.8 |
| 41 | 27 |
| 42 | 20 |
| Amantadine | 10 |

These figures show that compounds of the invention present a total inhibitory action on reserpine-induced and neuroleptic-induced catatonia at a dose which is proportionally twice as far from the toxic dose as in the case of amantadine. These compounds, consequently, possess a higher safety margin than that of amantadine.

In the case of 1,1-di-n-propyl-n-butylamine acid fumarate, the active dose is still farther removed from the toxic dose than in the case of Compound 1 as the corresponding index is (100/3≃33.

Additional trials were carried out on rats with Compound 1 and amantadine. These trails involved catalepsy as evidenced by the crossing of the animal's homolateral paws. It was observed in these trails that 5 mg/kg of Compound 1 when administered by oral route 30 minutes before an intraperitoneal injection of prochlorperazine provoked complete inhibition of the catalepsy 3 hours after the injection of this latter substance.

With regard to amantadine, a dose of 80 mg/kg was necessary to induce complete inhibition of the catalepsy.

The efficacy of Compound 1 in curative treatment was also demonstrated.

(a) Suppression of reserpine-induced catatonia

Batches of 5 male rats of the OFA strain, weighing 150 to 200 g were given 5 mg/kg of reserpine by intraperitoneal route. One hour and 45 minutes later, namely when the animals were in a state of catatonia, an aqueous dose of the compound to be studied was administered by oral route to all the animals with the exception of the control group.

The progress of the catatonia was then noted following the scale used in the tests described hereabove.

The maximum score was thus 5 per batch which means that all the animals of the batch were considered to be still in a state of catatonia.

The following results were obtained with Compound 1 in comparison with amantadine:

Table III

| | Time after administration of reserpine | | | | | | |
|---|---|---|---|---|---|---|---|
| | 2h | 2h15 | 2h30 | 3h | 3h30 | 4h | 5h |
| Controls | 5 | 5 | 5 | 3 | 3 | 1 | 2 |
| Compound 1 2.5 mg/kg | 4 | 3 | 2 | 0 | 0 | 0 | 0 |
| Compound 1 5 mg/kg | 5 | 1 | 0 | 0 | 0 | 0 | 0 |
| Amantadine 80 mg/kg | 5 | 4 | 3 | 2 | 1 | 0 | 0 |

These figures show that at doses of 2.5 mg/kg and 5 mg/kg, by oral route, Compound 1 suppresses reserpine-induced catatonia more rapidly than a dose of 80 mg/kg of amantadine administered under the same conditions.

Compound 1 is thus at least 32 times more active than amantadine with respect to reserpine-induced catatonia in curative treatment.

(b) Suppression of neuroleptic-incuded catatonia

Batches of 5 male rats of the OFA strain were given 12.5 mg/kg of prochlorperazine by intraperitoneal route. Fifty-five minutes later, an oral dose in aqueous solution of the compound to be studied was administered to all the animals with the exception of the control group. The progress of the catatonia was noted following the same scale as that used in the tests described above.

The following results were registered with Compound 1 as well as with amantadine:

Table IV

| | Time after administration of prochlorperazine | | | | | |
|---|---|---|---|---|---|---|
| | 1h30 | 2h30 | 3h | 3h30 | 4h | 5h |
| Controls | 4 | 4 | 4 | 3 | 1 | 1 |
| Compound 1 5 mg/kg | 3 | 0 | 0 | 0 | 0 | 0 |
| Amantadine 80 mg/kg | 5 | 2 | 1 | 0 | 0 | 0 |

These results show that under the conditions of curative treatment, a dose of 5 mg/kg of Compound 1 acts against neuroleptic-induced catatonia more rapidly than does a dose of 80 mg/kg of amantadine administered under the same conditions. In this test, Compound 1 is consequently at least 16 times more active than amantadine.

The toxico-pharmacological index, ($LD_{50}/ED_{50}$), is again more favourable to Compound 1 than to amantadine, i.e. 20 for Compound 1 and only 13 for amantadine.

A test was also carried out in order to determine whether Compound 1 possessed cholinolytic properties.

For this purpose, the MAGNUS test (Arch. gen. Physio. 1904, 102) was used. This test consists in determining the dose of acetylcholine which, when added to the bath, provokes spasm of the isolated duodenum of the rat. The next step consists in determining the dose of the compound under study which, when added to the bath 30 seconds before the acetylcholine, reduces the spasm.

The following results were recorded with Compound 1 in comparison with atropine:

Table V

|  | Doses in g/ml of bath | % of inhibition of the spasm |
|---|---|---|
| Acetylcholine | $0.5 \times 10^{-5}$ | — |
| Atropine | $0.1 \times 10^{-6}$ | 45 |
|  | $0.2 \times 10^{-6}$ | 100 |
| Compound 1 | $0.2 \times 10^{-6}$ | 0 |
|  | $0.1 \times 10^{-5}$ | 0 |
|  | $0.1 \times 10^{-4}$ | 0 |
|  | $0.1 \times 10^{-3}$ | 0 |
|  | $0.2 \times 10^{-2}$ | 36 |
|  | $0.5 \times 10^{-2}$ | 60 |

These results show that Compound 1 is 20,000 to 25,000 times less active than atropine.

The cholinolytic activity "in vitro" of Compound 1 may thus be considered as virtually non-existent in comparison with that of atropine.

The extremely weak cholinolytic action of Compound 1 must necessarily occur at toxic doses.

The absence of cholinolytic properties of Compound 1 was verified "in vivo" at therapeutic doses.

For this purpose, the following test was performed with a view to determining the anti-tremorine properties of Compound 1.

When injected into mice, tremorine produces peripheral effects i.e. weeping, sweating, salivation and diarrhoea and central effects i.e. tremor and akinesia. Such effects are due to an increase in the amount of intracerebral acetylcholine and serotonine.

Male mice of the $OF_1$ strain weighing about 22 g were divided into batches of 10. Each batch received, by oral route, 50 mg/kg of the compound to be tested in aqueous solution. Thirty minutes later a dose of 10 mg/kg of tremorine was injected by intraperitoneal route and, at different times after this injection, note was taken of the cholinergic effects on each animal in accordance with the following scale:
0: no action
1: slight action
2: average action
3: strong action
4: very strong action The results obtained with 5 mg/kg of Compound 1 and 40 mg/kg of amantadine were as follows:

With respect to the peripheral cholinergic effects i.e. salivation, sweating, and weeping, a score of 4 was registered for the control animals, 20, 30 and 40 minutes after the injection of tremorine for both 5 mg/kg of Compound 1 and 40 mg/kg of amantadine. Identical results were obtained with respect to the central cholinergic effects i.e. normal and provoked tremor.

These results show that Compound 1 and amantadine are devoid of antitremorine properties, which confirms the absence of cholinolytic properties in the case of Compound 1 at therapeutic doses.

Tests were also carried out with Compound 1 with a view to studying the influence of this compound on peripheral noradrenergic phenomena.

The following test was performed for this purpose:

A cat, anaesthetized with pentobarbital, received a sufficient dose of norepinephrine to increase arterial pressure but not sufficient to cause contraction of the nictitating membrane. Arterial pressure was measured at the carotid immediately after administration of the dose of norepinephrine. After this, increasing doses of Compound 1 in aqueous solution were administered by intravenous route every 30 minutes. After each dose of Compound 1, a further dose of norepinephrine was given and the following parameters were recorded: the increase in arterial pressure, the contractile reaction of the nictitating membrane due to exogenous norepinephrine as well as the contractil reaction of this membrane induced by the release of norepinephrine provoked by the sub-maximum electric stimulation of the cervical sympathetic nerve. The results listed hereunder were recorded with Compound 1 and amantadine:

Table VI

|  | Cumulative doses in mg/kg | Increase in arterial pressure in mm Hg after injection of norepinephrine | Contractile reaction of the nictitating membrane (in mm$^x$) | |
|---|---|---|---|---|
|  |  |  | Without electric stimulation | With electric stimulation |
| Compound 1 | 0 | 26 | 0 | 17 |
|  | 0.1 | 18 | 0 | 15 |
|  | 1 | 25 | 0 | 16 |
|  | 3 | 29 | 0 | 17 |
|  | 5 | 25 | 0 | 16 |
|  | 10 | 22 | 0 | 12 |
| Amantadine | 0 | 28 | 0 | 20 |
|  | 0.1 | 29 | 0 | 20 |
|  | 1 | 35 | 3 | 20 |
|  | 3 | 35 | 4.4 | 16 |
|  | 5 | 59 | 5.9 | 10 |
|  | 10 | 57 | 7.5 | 4 |

These results show that Compound 1 does not potentiate the effects either of exogenous norepinephrine or of endogenous norepinephrine.

Amantadine, on the other hand; potentiates exogenous norepinephrine from 1 mg/kg, since it increases the intensity and duration of the hypertensive effects of this amine and, after it has been administered, a dose of norepinephrine which would otherwise have no effect on the membrane provokes, on the contrary, a contractile reaction on the part of the latter.

Furthermore, amantadine itself stimulates the contractile reactions of the nictitating membrane but does not potentiate the effects of the electric stimulation. On the contrary, amantadine shows ganglioplegic properties from 5 mg/kg.

It will be appreciated that for therapeutic use the compounds of the invention will normally be administered in the form of a pharmaceutical or veterinary composition in a dosage unit form appropriate to the required mode of administration, the composition comprising as active ingredient a compound of the invention in association with a pharmaceutical carrier or excipient therefor. For oral administration, the composition may take the form of, for example, a coated or uncoated tablet, a hard- or soft-gelatin capsule, a suspension or a syrup. The composition may alternatively take the form of a suppository for rectal administration, or of a solution or suspension for parenteral administration.

When in dosage unit form the composition may contain from 5 to 50 mg, preferably from 5 to 20 mg of the active ingredient per dosage unit for oral administration, from 5 to 100 mg of the active ingredient per dosage unit for rectal administration, or from 1 to 20 mg of the active ingredient per dosage unit for parenteral administration.

The therapeutic compositions of the invention will be prepared by associating at least one of the compounds of formula I or a pharmaceutically acceptable acid addition salt thereof with at least one appropriate carrier or excipient therefor. Examples of suitable carriers or excipients are talc, magnesium stearate, milk sugar, saccharose, carboxymethylcellulose, starches, kaolin, levilite and cocoa butter.

The following Examples illustrate the preparation of the compounds of the invention together with a suitable therapeutic composition:

EXAMPLE 1

Preparation of 1,1-di-n-propyl-n-butylamine hydrochloride or tri-n-propylmethylamine hydrochloride (a) 1,1-Di-n-propyl-n-butylisocyanate In a 2-liter three-necked flask fitted with a water condenser, a mechanical stirrer, a thermometer and a dropping-funnel were placed 144 g of sodium hydroxide in tablet form and 1200 ml of water. The solution was cooled to 5° C. and, under stirring, 48 ml of bromine were slowly added. The operation of adding the bromine lasted two hours and then, at a temperature of 0° C., 111 g of 2,2-di-n-propyl-valeramide were added to the yellowish-green solution. Stirring of the mixture was maintained at about 0° C. for 4 hours. The oily phase was then extracted with three fractions of ether each of 300 ml and the ethereal phase was washed twice with 100 ml of water, dried over magnesium sulphate and evaporated under vacuum. The light yellow oil so obtained was distilled under reduced pressure of 5 mmHg.

In this manner 105 g of colourless 1,1-di-n-propyl-n-butylisocyanate were obtained.

B.P. 78°–79° C. under 5 mmHg.

Yield: 95%

By following the same procedure as that described hereabove by using the appropriate starting-products, the compounds hereunder were prepared:

| Compounds | Boiling point °C. |
|---|---|
| 1,1-Di-n-butyl-n-pentylisocyanate | 92–93 (0.5 mmHg) |
| (Yield : 80%) | |
| 1-n-Propyl-1-isopropyl-n-butylisocyanate | 97 |

| Compounds | Boiling point °C. |
|---|---|
| | (15 mmHg) |

(b) 1,1-Di-n-propyl-n-butylamine hydrochloride

Into a three-necked flask equipped with a mechanical stirrer, a dropping-funnel, a thermometer and a condenser, were introduced 200 ml of water and 90 ml of concentrated hydrochloric acid (d=1.19). The acid solution was heated to 90° C. and then, under vigorous stirring, 105 g of 1,1-di-n-propyl-n-butylisocyanate, prepared as previously described, were slowly added. The operation of addition lasted one hour after which the reaction medium was heated for a further 4 hours at a temperature between about 95° and 100° C. The mixture was then cooled to about 0° C. and the colourless crystals so obtained were filtered off dried by exposure to the air and then in a dessicator in the presence of potassium hydroxide. In this manner, 99 g of 1,1-di-n-propyl-n-butylamine hydrochloride were isolated in the form of a white crystalline powder.

The product does not melt but sublimates from 220° C.

Yield: 90%

By following the same procedure as that described hereabove but using the appropriate starting-products, the compounds hereunder were obtained:

| Compound | |
|---|---|
| 1,1-Di-n-butyl-n-pentylamine hydrochloride (Yield : 63%) | M.P. 68.1° C. |
| 1-Ethyl-1-n-propyl-n-butylamine hydrochloride | 180° C. (sublimation) |
| 1-Ethyl-1-isobutyl-n-butylamine hydrochloride | 230° C. (sublimation) |
| 1-n-Propyl-1-isobutyl-n-butylamine hydrochloride | M.P. 260° C. |
| 1-Ethyl-1-n-propyl-n-pentylamine hydrochloride | M.P. 230° C. (decomposition) |
| 1-n-Propyl-1-isopropyl-n-butylamine hydrochloride | M.P. 260° C. (decomposition) |

EXAMPLE 2

Preparation of 1,1-di-n-propyl-n-butylamine and fumarate

To a solution of 1.16 g (0.01 mol) of fumaric acid in 20 ml of acetone, were slowly added 1.57 g (0.01 mol) of 1,1-di-n-propyl-n-butylamine ($n_D^{21}=1.4349$) dissolved in 10 ml of acetone, this amine having being prepared from its hydrochloride and a 30% aqueous solution of sodium hydroxide. The mixture was stirred for one hour and then the crystals which formed were suction-filtered, washed with acetone and dried under vacuum.

In this manner, 1,1-di-n-propyl-n-butylamine acid fumarate was obtained in the form of a white powder.

M.P. 216° C. with sublimation

Yield: 100%

EXAMPLE 3

Preparation of 1-n-propyl-1-isobutyl-n-butylamine hydrochloride (a) 1-n-Propyl-1-isobutyl-n-butanol Into a 250 ml three-necked flask equipped with a mechanical stirrer a nitrogen inlet, a dropping-funnel and a thermometer, were introduced under nitrogen atmosphere 2.8 g (0.2 mol) of lithium in small portions and 100 ml of anhydrous and purified tetrahydrofuran. The suspension of lithium in tetrahydrofuran was cooled to −20° C. and then while stirring a mixture of 22.8 g (0.2 mol) of di-n-propylketone and 30 g (0.2 mol plus a 10% excess) of isobutyl bromide were slowly added. The operation of addition lasted about 3 hours during which time a temperature of about −20° C. was maintained. The solution was allowed to stand for about 12 hours at room temperature and then concentrated. The oil so obtained was taken up in water, extracted with ether and distilled under reduced pressure.

In this manner, 21 g of 1-n-propyl-1-isobutyl-n-butanol were obtained in the form of a clear liquid which was slightly yellow.

B.P. 74°–76° under 5 mmHg.
Yield: about 60%

Following the same procedure as that described above but using the appropriate starting-products, the compounds listed hereunder were prepared:

| Compound | Boiling point °C. |
| --- | --- |
| 1,1-Diethyl-n-butanol | 62 |
| | (15 mmHg) |
| (Yield : 50%) | |
| 1-Ethyl-1-n-propyl-n-butanol | 178–179 |
| (Yield : 35%) | (760 mmHg) |
| 1-Ethyl-1-isobutyl-n-butanol | 78–79 |
| (Yield : 40%) | (15 mmHg) |
| 1,1-Di-n-propyl-n-butanol | 78–80 |
| (Yield : 60%) | (0.15 mmHg) |
| 1-n-Propyl-1-isopropyl-n-butanol | 81 |
| | (15 mmHg) |
| 1-n-Propyl-1-tert-butyl-n-butanol | 90–92 |
| | (14 mmHg) |
| 1,1-Dimethyl-n-octanol | 93–95 |
| (Yield : 45%) | (13 mmHg) |
| 1,1,3-Trimethyl-n-heptanol | Decomposition |
| (Yield : 60%) | |
| 1,1-Dimethyl-3-ethyl-n-hexanol | Decomposition |
| (Yield : 30%) | |
| 1,3-Dimethyl-1-ethyl-n-hexanol | Decomposition |
| (Yield : 35%) | |
| 1,3-Dimethyl-1-n-propyl-n-pentanol | Decomposition |
| (Yield : 46%) | |
| 1-Methyl-1-isobutyl-n-pentanol | Decomposition |
| (Yield : 33%) | |
| 1-Methyl-1-n-propyl-n-hexanol | Decomposition |
| (Yield : 30%) | |
| 1,1-Diisobutyl-n-butanol | 75–76 |
| (Yield : 60%) | (4 mmHg) |
| 1-Ethyl-1-n-propyl-n-pentanol | 87 |
| (Yield : 35%) | (11 mmHg) |

(b) 1-n-Propyl-1-isobutyl-n-butylamine hydrochloride

Into a 250 ml three-necked flask equipped with a mechanical stirrer, a dropping-funnel, a condenser and a dip thermometer, were introduced 6.5 g (0.1 mol) of dry potassium cyanide in powder form, 14.4 g (0.083 mol) of 1-n-propyl-1-isobutyl-n-butanol and 12 ml of acetic acid. While stirring, a mixture of 25 g of concentrated sulphuric acid (d=1.83) and 12 ml of acetic acid was slowly added. The operation of addition lasted about 2 hours during which time a temperature of about 50° C. was maintained. The reaction mixture was heated to 70° C. for 2 hours and was then slowly poured into 100 ml of iced water. After this, it was neutralized with a 20% aqueous solution of sodium hydroxide and extracted with ether. The ether was evaporated out and an oil comprising N-formylated 1-n-propyl-1-isobutyl-n-butylamine was collected.

The N-formylated amine thus obtained was refluxed for 2 hours in the presence of 20 ml of concentrated hydrochloric acid. While cooling, the hydrochloride of this amine crystallized. It was then filtered off and washed with acetone.

In this manner, 11 g of 1-n-propyl-1-isobutyl-n-butylamine hydrochloride was collected in the form of a white powder. M.P.>260° C. with decomposition without melting at about 280° C.

Yield: 64%

In a thin layer chromatographic assay performed on silicagel plates (Merck HF 254) using a system of solvents comprising 79 parts of benzene, 14 parts of methanol and 7 parts of acetic acid and with iodine as revealing agent, a Rf of 0.6 was recorded.

Following the same procedure as that described hereinabove but using the appropriate starting-products, the compounds listed hereunder were prepared. The Rf value given for each of these compounds was determined in a thin layer chromatographic assay using the same support, the same system of solvents and the same revealing agent as those mentioned in the Example hereabove described:

| Compound | |
| --- | --- |
| 1,1-Diethyl-n-propylamine hydrochloride | 210° C. |
| (Yield : 40%) | (sublimation) |
| Rf = 0.49 | |
| 1,1-Di-n-propyl-n-butylamine hydrochloride | 220° C. |
| | (sublimation) |
| 1,1-Diethyl-n-butylamine hydrochloride | M.P. > 300° C. |
| (Yield : 60%) | |
| Rf = 0.59 | |
| 1-Ethyl-1-n-propyl-n-butylamine hydrochloride | 180° C. |
| (Yield : 25%) | (sublimation) |
| Rf = 0.64 | |
| 1-Ethyl-1-isobutyl-n-butylamine hydrochloride | 230° C. |
| (Yield : 30%) | (sublimation) |
| Rf = 0.60 | |
| 1,1-Dimethyl-n-octylamine hydrochloride | M.P. 111.8° C. |
| (Yield : 45%) | |
| Rf = 0.65 | |
| 1,3-Dimethyl-1-ethyl-n-hexylamine hydrochloride | M.P. 133.3° C. |
| Rf = 0.56 | |
| 1-Methyl-1-n-propyl-n-hexylamine hydrochloride | M.P. 174.7° C. |
| (Yield : 60%) | |
| Rf = 0.60 | |
| 1-n-Propyl-1-isopropyl-n-butylamine hydrochloride | M.P. 260° C. (Decomposition) |
| 1-Ethyl-1-n-propyl-n-pentylamine hydrochloride | M.P. 230° C. |
| (Yield : 30%) | (Decomposition) |
| Rf = 0.60 | |

EXAMPLE 4

Preparation of 1,1-dimethyl-3-ethyl-n-hexylamine acid fumarate (a) 1,1-Dimethyl-3-ethyl-n-hexylamine 1,1-Dimethyl-3-ethyl-n-hexylamine in free base form was first prepared by reacting a 30% aqueous solution of sodium hydroxide with 1,1-dimethyl-3-ethyl-n-hexylamine hydrochloride. The free base so obtained was then extracted with ether.

(b) 1,1-Dimethyl-3-ethyl-n-hexylamine acid fumarate

To a solution of 1.74 g (0.015 mol) of fumaric acid in 300 ml of acetone were slowly added 2.3 g (0.015 mol) of 1,1-dimethyl-3-ethyl-n-hexylamine, prepared as previously described in 40 ml of acetone. The mixture was stirred for 3 hours and the fumarate which crystallized was filtered off, washed with acetone and dried.

In this manner, 2 g of 1,1-dimethyl-3-ethyl-n-hexylamine acid fumarate were obtained in the form of colourless crystals.

M.P. 160.6° C.
Yield: 50%

In a thin layer chromatographic assay performed on silicagel plates (Merck HF 254) using a system of solvents comprising 79 parts of benzene, 14 parts of methanol and 7 parts of acetic acid and with iodine as revealing agent, a Rf of 0.56 was recorded.

By following the same procedure as that described above but using the appropriate starting-products, the compounds listed hereunder were prepared.

The Rf value given for each of these compounds was determined in a thin layer chromatographic assay using the same support, the same system of solvents and the same revealing agent as those mentioned in the Example hereabove described:

| Compound | |
|---|---|
| 1,1,3-Trimethyl-n-heptylamine acid fumarate Rf = 0.54 | M.P. 140° C. |
| 1-n-Propyl-1-tert-butyl-n-butylamine acid fumarate | 180° C. (sublimation) |
| 1,3-Dimethyl-1-n-propyl-n-pentylamine acid fumarate Rf = 0.56 | M.P. 114.4° C. |
| 1,1-Diisobutyl-n-butlyamine acid fumarate Rf = 0.66 | M.P. 179° C. |

EXAMPLE 5

Preparation of 1-methyl-1-isobutyl-n-pentylamine neutral fumarate (a) 1-Methyl-1-isobutyl-n-pentylamine 1-Methyl-1-isobutyl-n-pentylamine in free base form was first prepared by reacting a 30% aqueous solution of sodium hydroxide with 1-methyl-1-isobutyl-n-pentylamine hydrochloride.

The free base so obtained was then extracted with ether.

(b) 1-Methyl-1-isobutyl-n-pentylamine neutral fumarate

While stirring, the amine in free base form so obtained was slowly added to a solution of 2.32 g (0.02 mol) of fumaric acid in 300 ml of acetone. The fumarate slowly crystallized. Stirring was maintained for further hour and the crystals which formed were filtered off, washed with acetone and dried.

In this manner, 3.1 g of 1-methyl-1-isobutyl-n-pentylamine neutral fumarate were obtained in the form of colourless crystals.

M.P. 198.4° C.
Yield: 70%
Rf=0.58 (in a thin layer chromatographic assay using the same solvents and revealing agent as in Examples 2 and 3 above).

EXAMPLE 6

Preparation of 1-ethyl-1-n-propyl-n-pentylamine hydrochloride (a) 2-Ethyl-2-n-propyl-hexanoic acid Into a three-necked flask fitted with a mechanical stirrer, a thermometer and two dropping-funnels, were placed 204 g of 96% sulphuric acid cooled to 5° C. and 4 ml of formic acid. While maintaining the mixture at a temperature of about 10° C., 23 g (0.5 mole) of formic acid and 15.8 g (0.1 mol) of 1-ethyl-1-n-propyl-n-pentanol in 100 ml of pentane were simultaneously added. The operation of addition lasted 40 minutes after which the reaction mixture was allowed to return to room-temperature in 2 hours. The mixture was poured onto 100 g of crushed ice and the acid was extracted with ether. The acid was purified by preparing its sodium salt with a 20% aqueous solution of sodium hydroxide. The aqueous phase was acidified with 50% hydrochloric acid and extracted with ether.

The organic fraction was then dried over magnesium sulphate and concentrated under vacuum.

In this manner, 2-ethyl-2-n-propyl-hexanoic acid was obtained in the form of a colourless liquid.

B.P. 130°–132° C. under 20 mmHg
Yield: about 20%

Using the same method as that described above, the following compound was prepared:

| Compound | B.P. |
|---|---|
| 2-Ethyl-2-n-propyl-pentanoic acid | 122° C. (12 mmHg) |

(b) 1-Ethyl-1-n-propyl-n-pentylamine

Into a three-necked flask equipped with a mechanical stirrer and a condenser, were introduced 70 ml of chloroform, 18 ml of concentrated sulphuric acid (d=1.83) and 11 g (0.06 mol) of 2-ethyl-2-n-propylhexanoic acid prepared as described above. The mixture was heated to 50° C. and while stirring 7.5 g of sodium azide in powder form were added. The operation of addition lasted 90 minutes after which the reaction mixture was heated to 50° C. for 2 hours. The mixture was then neutralized with a 40% aqueous solution of sodium hydroxide previously cooled to 0° C. The amine was extracted with ether and the ethereal phase was washed with water and dried over magnesium sulphate. The ether was evaporated out under vacuum and the oil so obtained was taken up in dry ether, which provided 1-ethyl-1-n-propyl-n-pentylamine in free base form.

Using the same method as that described above, the following compound was prepared:

| Compound | B.P. |
|---|---|
| 1,1-Di-n-propyl-n-butylamine | 190.5–195° C. (742 mmHg) |

(c) 1-Ethyl-1-n-Propyl-n-pentylamine hydrochloride

The hydrochloride of the amine, previously obtained, was precipitated by bubbling dry gaseous hydrochloric acid through the solution of the said amine.

In this manner, 1-ethyl-1-n-propyl-n-pentylamine hydrochloride was obtained in the form of colourless crystals which sublimated from 200° C.

Yield: 45%

By following the same procedure as that described above, the following compounds were prepared:

| Compound | |
|---|---|
| 1,1-Di-n-propyl-n-butylamine hydrochloride | 220° C. (sublimation) |
| 1-Ethyl-1-n-propyl-n-butylamine hydrochloride | 180° C. (sublimation) |
| 1-Ethyl-1-isobutyl-n-butylamine hydrochloride | 230° C. (sublimation) |
| 1-n-Propyl-1-isobutyl-n-butylamine hydrochloride | M.P. 260° C. |
| 1-n-Propyl-1-isopropyl-n-butylamine hydro- | M.P. 260° C. |

-continued

| Compound | |
|---|---|
| chloride | (decomposition) |
| 1,1-Di-n-propyl-3-butyn-1-ylamine hydrochloride | 262° C. (sublimation and decomposition) |

EXAMPLE 7

Preparation of 1,1-di-(2-propen-1-yl)-3-buten-1-ylamine oxalate (a) 1,1-Di-(2-propen-1-yl)-3-buten-1-ylamine (or triallylmethylamine)

Under nitrogen atmosphere, 13.4 g (0.2 mol) of allyl cyanide in 20 ml of dry ether were added to a solution of 0.4 mol of allyl magnesium bromide in 350 ml of ether. The operation of addition lasted one hour while the ether was lightly refluxed. After this, the reaction medium was heated to boiling for 4 hours. After cooling, the mixture was poured into 200 ml of a saturated solution of ammonium chloride. The ethereal phase was separated out, washed with water, dried over magnesium sulphate and evaporated under vacuum. The oil so obtained was distilled under reduced pressure.

In this manner, 14 g of 1,1-di-(2-Propane-1-yl)-3-buten-1-ylamine were obtained in the form of a slightly yellow liquid.

B.P. 79°–80° C. (under 15 mmHg)
Yield: 46%

By following the same procedure as that described above the following compound was prepared:

| Compound | |
|---|---|
| 1,1-Di-n-propyl-n-butylamine | $n_D^{21} = 1.4349$ |

(b) 1,1-Di-(2-propen-1-yl)-3-buten-1-ylamine oxalate

While stirring, 3 g (about 0.02 mol) of 1,1-di-(2-propen-1-yl)-3-buten-1-ylamine, prepared as described above, in 20 ml of ether were added to 2.5 g (about 0.02 mol) of hydrated oxalic acid (2 molecules of hydration water) in 300 ml of ether.

Stirring was maintained for 30 minutes and then the colourless crystals which precipitated were filtered out. The crystals were washed with ether and recrystallized from ethyl acetate.

In this manner, 4 g of 1,1-di-(2-propen-1-yl)-3-buten-1-ylamine oxalate were obtained.
M.P. 96.2° C.
Yield: 70%

By following the same procedure as that described above but using hydrochloric acid in place of oxalic acid, the following compound was prepared:

| Compound | |
|---|---|
| 1,1-Di-n-propyl-n-butylamine hydrochloride | 220° C. (sublimation) |

EXAMPLE 8

Preparation of 1,1-di-n-propyl-2-propyn-1-ylamine hydrochloride (a) 1,1-Di-n-propyl-2-propyn-1-ol A 2-liter three-necked flask fitted with a mechanical stirrer, a condenser, a dip tube and a dropping-funnel was placed in a fume cupboard. Into the flask previously cooled in a bath of carbon-dioxide snow in acetone, was introduced 1 liter of liquid ammonia. Acetylene, previously purified by passing through a trap containing carbon-dioxide snow, bubbling in a sulphuric acid solution and drying over caustic potash, was then bubbled through the rection medium.

To the acetylene solution in ammonia were added 23 g of finely divided sodium. The bubbling of acetylene was maintained for 1 hour after the introduction of the sodium. After that, 114 g (1 mol) of di-n-propyl ketone were added and the acetylene flow was maintained for 1 hour after which 500 ml of ether were added and the mixture was allowed to stand for 12 hours at room-temperature. It was then hydrolysed by adding damp ether followed by crushed ice. After acidification with 10% sulphuric acid, the ethereal phase was separated out, dried over magnesium sulphate and concentrated under reduced pressure.

In this manner, 45 g of 1,1-di-n-propyl-2-propyn-1-ol were collected after distillation, which represents a yield of 32%.

B.P. 68°–70° C.

(b) 1,1-Di-n-propyl-1-chloro-2-propyne

Into a 3-necked flask fitted with a magnetic stirrer, a thermometer and a dropping-funnel, were placed 6.5 g of freshly prepared cuprous chloride, 9.1 g of calcium chloride, 0.020 g of copper-bronze powder and 71 ml of concentrated and iced hydrochloric acid (d=1.19). While stirring, 23 g of 1,1-di-n-propyl-2-propyn-1-ol, prepared as described above were added to the mixture maintained at 10° C.

The operation of adding the alcohol lasted 30 minutes and then the reaction mixture was allowed to stand for 2 hours at room-temperature. The supernating part of the mixture was decanted into a dropping-funnel and washed with twice 15 ml of concentrated and iced hydrochloric acid and then with three times 20 ml of distilled water. After drying over potassium carbonate, the mixture was distilled to give the desired product.

In this manner, 17 g of 1,1-di-n-propyl-1-chloro-2-propyne in the form of a limpid and colourless liquid were obtained which represents a yield of 65%.

B.P. 63°–65° C. under 14 mm Hg.

(c) 1,1-Di-n-propyl-2-propyn-1-ylamine

To a suspension of sodium amide in liquid ammonia, prepared from 6.9 g of sodium and 250 ml of liquid ammonia, were added 17 g of 1,1-di-n-propyl-1-chloro-2-propyne in 50 ml of anhydrous ethyl ether. The operation of adding the chlorinated derivative lasted one hour. Stirring of the mixture was maintained for 2 hours and then 300 ml of anhydrous ethyl ether were added.

The reaction medium was allowed to stand for 12 hours after which the ammonia was evaporated off and 100 g of crushed ice were added. The ethereal phase was separated out and the basic phase was extracted with 300 ml of a 10% aqueous solution of hydrochloric acid. The amine was recovered by adding concentrated and iced caustic soda and again extracting with ether.

In this manner, 1,1-di-n-propyl-2-propyn-1-ylamine was obtained in the form of its free base.

By following the same method as that described above, the compounds listed below were prepared:

| Compound | |
|---|---|
| 1,1-Dimethyl-2-propyn-1-ylamine | M.P. 18° C. |
| 1,1-Diethyl-2-propyn-1-ylamine | B.P. 71°–72° C. |

| Compound | |
|---|---|
| | (90 mmHg) |

(d) 1,1-Di-n-propyl-2-propyn-1-ylamine hydrochloride

The ethereal solution of amine previously obtained was dried over magnesium sulphate and the hydrochloride of this amine was then precipitated by bubbling dry gaseous hydrochloric acid. The crystals so obtained were separated out and dried in a dessicator in the presence of caustic potash.

In this manner, 12 g of 1,1-di-n-propyl-2-propyn-1-ylamine hydrochloride were obtained in the form of colourless crystals, which represents a yield of 68%. M.P. 200° C. (with decomposition).

EXAMPLE 9

Preparation of 1,1-diethyl-2-pentyn-1-ylamine hydrochloride (a) 1,1-Diethyl-2-pentyn-1-ylamine Into a 3 necked-flask fitted with a mechanical stirrer, a vertical condenser and a dropping-funnel, was prepared a suspension of sodium amide from 150 ml of liquid ammonia, 2.4 g of sodium and some crystals of ferric nitrate. To this suspension, was added, in 30 minutes, a solution of 11 g of 1,1-diethyl-2-propyn-1-ylamine, prepared as previously described, and 20 ml of anhydrous ethyl ether. When the operation of addition was finished, the stirring of the mixture was maintained for 30 minutes and a solution of 15 g of dry ethyl bromide in 30 ml of anhydrous ethyl ether was introduced drop-by-drop into the reaction mixture. The operation of adding the ethyl bromide lasted one hour, after which stirring of the mixture was maintained for 4 hours. The reaction medium was then allowed to stand for 12 hours so that the ammonia could evaporate and 50 g of crushed ice were added. The ethereal phase was separated out, dried over magnesium sulphate and then evaporated out under reduced pressure.

In this manner, 8 g of 1,1-diethyl-2-pentyn-1-ylamine were obtained, after distillation, in the form of a colourless liquid.

B.P. 62°–63° C. under 15 mm Hg.

Yield: 57%

By following the same procedure as that described above but using the appropriate starting-products, the following compound was prepared:

| Compound | B.P. |
|---|---|
| 1,1-Di-n-propyl-2-pentyn-1-ylamine (Yield : 55%) | 92°–94° C. (15 mmHg) |

(b) 1,1-Diethyl-2-pentyn-1-ylamine hydrochloride

The hydrochloride of the amine previously obtained was prepared by treating an anhydrous ethereal solution of this amine with dry gaseous hydrochloric acid. By evaporating the ether and drying the crystals so obtained in a dessicator and in the presence of caustic potash, 1,1-diethyl-2-pentyn-1-ylamine hydrochloride was obtained in the form of a white powder.

M.P. 85° C.

Yield: 100%

By following the same procedure as that described above, the following compound was prepared:

| Compound | M.P. |
|---|---|
| 1,1-Di-n-propyl-2-pentyn-1-ylamine hydrochloride (Yield : 100%) | 118° C. |

EXAMPLE 10

Preparation of 1,1-diethyl-2-penten-1-ylamine hydrochloride

In 40 ml of heptane, 3.5 g of 1,1-diethyl-2-pentyn-1-ylamine were hydrogenated in the presence of 50 mg of a Lindlar catalyst (catalyst formed from palladium, sodium carbonate and lead oxide). The addition of hydrogen on the triple bond was facilitated by maintaining the mixture under stirring and heating it to a temperature of about 50° C. The absorption of 560 cm$^3$ of hydrogen was achieved in 90 minutes. After evaporating the solvent, the desired hydrochloride was isolated by adding dry gaseous hydrochloric acid. The crystals so obtained were dried in a dessicator in the presence of caustic potash.

In this manner, 1,1-diethyl-2-penten-1-ylamine hydrochloride was obtained in the form of a white powder.

M.P. 200° C. with sublimation.

Yield: 100%

By following the same procedure as that described above, the following compound was prepared:

| Compound | |
|---|---|
| 1,1-Di-n-propyl-2-penten-1-ylamine hydrochloride (Yield : 100%) | 200° C. (sublimation) |

EXAMPLE 11

Preparation of N-methyl-1,1-di-n-propyl-n-butylamine hydrochloride (a) N-Methyl-1,1-di-n-propyl-n-butylamine To a suspension of 1.9 g (0.05 mol) of lithium aluminium hydride in 60 ml of anhydrous sulphuric ether was added a solution of 3.66 g (0.02 mol) of 1,1-di-n-propyl-n-butylisocyanate in 20 ml of dry ether. The operation of addition was carried out over a period of 30 minutes at room-temperature after which the reaction medium was heated under reflux for 3 hours. After hydrolysis, first with ether saturated with water and then with water, the organic fraction was separated out. The organic phase was dried over magnesium sulphate and distilled under reduced pressure.

In this manner, 3.2 g of N-methyl-1,1-di-n-propyl-n-butylamine were obtained in the form of a colourless liquid.

B.P.: 84° C. under 13 mm Hg.

Yield: 94%

(b) N-Methyl-1,1-di-n-propyl-n-butylamine hydrochloride

By bubbling dry gaseous hydrogen chloride through the ethereal solution of the amine previously obtained, N-methyl-1,1-di-n-propyl-n-butylamine hydrochloride was precipitated in the form of colourless crystals.

M.P.: 133°–134° C.

Yield: 90%

By following the same procedure as that described hereabove but using the appropriate starting-products, the compound hereunder was prepared:

| Compound | Melting point °C. |
|---|---|
| N-Methyl-1-n-propyl-1-isopropyl-n-butylamine (Yield : 80%) | 144–145 |

EXAMPLE 12

Preparation of
N-methyl-1,1-di-n-propyl-3-buten-1-ylamine fumarate

First 1,1-di-n-propyl-3-buten-1-yl isocyanate was prepared by reacting bromine and 2,2-di-n-propyl-4-pentenoamide in the presence of sodium hydroxide. The desired product was obtained in the form of a colourless liquid boiling at 79°–82° C. under 5 mm Hg. The isocyanate so obtained was then reduced by means of lithium aluminium hydride to provide, without purification, N-methyl-1,1-di-n-propyl-3-buten-1-ylamine in a yield of 89%.

To a solution of 2.32 g (0.02 mol) of fumaric acid in 400 ml of acetone, were added under stirring 3.38 g (0.02 mol) of the amine, prepared hereabove, dissolved in 30 ml of acetone.

Stirring was maintained for one hour after which the colourless crystals which precipitated were separated out. They were washed with acetone and dried.

In this manner, 5.2 g of N-methyl-1,1-di-n-propyl-3-buten-1-ylamine fumarate were obtained.

M.P.: 149° C.
Yield: 91%

EXAMPLE 13

Preparation of
N-methyl-1-n-propyl-1-isobutyl-n-butylamine hydrochloride (a) N-Methyl-1-n-propyl-1-isobutyl-n-butylamine In a one-liter three-necked flask, equipped with a condenser of the Dean Stark type, were placed 30 g (0.175 mol) of 1-n-propyl-1-isobutyl-n-butylamine, 150 ml of 30% formol and 400 ml of benzene. The mixture was refluxed for 5 hours so as to eliminate by azeotropic distillation about 100 ml of water. After evaporating the benzene under vacuum, the oil so obtained was taken up in 250 ml of methanol and, at a temperature of 10° C., 13.3 g (0.35 mol) of sodium borohydride were added by small fractions. The temperature of the mixture was maintained at 10° C. during the operation of addition of the hydride and stirring was maintained for 30 minutes at this temperature. The reaction medium was refluxed for one hour and the methanol was then evaporated off under vacuum. To the product so obtained, 200 ml of distilled water and 100 ml of a concentrated solution of sodium hydroxide were added. The organic fraction was extracted with ether and dried over magnesium sulphate. The ether was evaporated out under vacuum and the residual liquid was distilled using a column.

In this manner, 11 g of N-methyl-1-n-propyl-1-isobutyl-n-butylamine were obtained in the form of a colourless liquid.

B.P.: 86° C. under 12 mm Hg
Yield: 34%

(b) N-Methyl-1-n-propyl-1-isobutyl-n-butylamine hydrochloride

In 150 ml of absolute ethanol, 10.4 g of the amine previously obtained were dissolved and the resulting solution was treated by means of 5.6 ml of concentrated hydrochloric acid and evaporated to dryness.

The oil so obtained was taken up in 50 ml of hexane and the desired hydrochloride crystallized when cold. It was separated out and recrystallized in isopropyl ether. In this manner, 7.5 g of N-methyl-1-n-propyl-1-isobutyl-n-butylamine hydrochloride were obtained.

Yield: 61%
M.P.: 139° C.

By following the same procedure as that described hereabove but using the appropriate starting-products, the compound hereunder was prepared:

| Compound | M.P. °C. |
|---|---|
| N-Methyl-1,1-di-n-propyl-n-butylamine hydrochloride | 133–134 |

EXAMPLE 14

Preparation of
N-ethylidene-1,1-di-n-propyl-n-butylamine

Into a 25-ml two-necked flask, were introduced 7.9 g (0.05 mol) of 1,1-di-n-propyl-n-butylamine. To this product, 2.64 g (0.06 mol) of acetaldehyde were added slowly, the reaction medium being cold. After this operation, 5.6 g of potassium hydroxide in pellet form were introduced and stirring was maintained for one hour at room-temperature. The lower phase was separated out from the organic phase which was distilled under vacuum in the presence of 1 g of ground potassium hydroxide and under nitrogen atmosphere.

In this manner, 7.8 g of N-ethylidene-1,1-di-n-propyl-n-butylamine were obtained in the form of a colourless liquid.

B.P.: 87° C. under 13 mm Hg
Yield: 85%

EXAMPLE 15

Preparation of N-ethyl-1,1-di-n-propyl-n-butylamine hydrochloride (a) N-Ethyl-1,1-di-n-propyl-n-butylamine Into a 500-ml three-necked flask, fitted with a mechanical stirrer and a condenser, were introduced 17.6 g (0.096 mol) of N-ethylidene-1,1-di-n-propyl-n-butylamine, prepared as described hereabove, and 150 ml of methanol. To this solution when cooled, 7.6 g (0.2 mol) of sodium borohydride were added slowly and while stirring. After this operation, the mixture was maintained at a temperature of 5° C. for 30 minutes and then progressively heated under reflux. Thirty minutes later, the methanol was evaporated off under vacuum and 200 ml of water were added to the residue so obtained followed by 100 ml of a solution of sodium hydroxide (d=1.38). The organic fraction was extracted with ether and the solution was distilled under reduced pressure.

In this manner, 11.8 g of N-ethyl-1,1-di-n-propyl-n-butylamine were collected in the form of a colourless liquid.

B.P.: 80°–81° C. under 11 to 12 mm Hg
Yield: 69%

(b) N-Ethyl-1,1-di-n-propyl-n-butylamine hydrochloride

By bubbling dry gaseous hydrogen chloride through an ethereal solution of the amine previously prepared, N-ethyl-1,1-di-n-propyl-n-butylamine hydrochloride precipitated.

M.P.: 190°–191° C.
Quantitative yield.

EXAMPLE 16

Preparation of N-ethyl-1,1-di-n-propyl-n-butylamine hydrochloride (a) N-Acetyl-1,1-di-n-propyl-n-butylamine To a solution of 7.85 g (0.05 mol) of 1,1-di-n-propyl-n-butylamine in 5.3 g of pyridine, 3.9 g of acetyl chloride were slowly added. The mixture was heated to 80° C. for 3 hours and then poured into 60 ml of iced water. The precipitate so obtained was separated out, washed with water and dried.

In this manner, 7 g of N-acetyl-1,1-di-n-propyl-n-butylamine were obtained after recrystallization from heptane.

M.P.: 91° C.
Yield: 70%.

(b) N-Ethyl-1,1-di-n-propyl-n-butylamine hydrochloride

To a suspension of 1.9 g of lithium aluminium hydride in 80 ml of butyl ether, were added, while stirring, 4 g (0.02 mol) of the N-acetylate derivative previously obtained, dissolved in 20 ml of butyl ether. The mixture was progressively heated under reflux which was maintained for 5 hours. After hydrolysis by adding ice, the ethereal fraction was separated out and washed twice with 70 ml of a 10%-hydrochloric acid solution. From the aqueous fraction, the hydrochloride of the desired amine was extracted with methylene chloride and the solution evaporated under vacuum.

In this manner, 3 g of N-ethyl-1,1-di-n-propyl-n-butylamine hydrochloride were obtained in the form of colourless crystals.

M.P.: 190°–191° C.
Yield: 67%

By following the same procedure as that described hereabove but using the appropriate starting products, the compound hereunder was prepared:

| Compound | M.P. °C. |
| --- | --- |
| N-Methyl-1,1-di-n-propyl-n-butylamine hydrochloride | 133–134 |

EXAMPLE 17

Preparation of N-n-propyl-1,1-di-n-propyl-n-butylamine hydrochloride (a) N-Propionyl-1,1-di-n-propyl-n-butylamine To a solution of 7.85 g (0.05 mol) of 1,1-di-n-propyl-n-butylamine and 5.3 g of 2,6-dimethyl-pyridine in 100 ml of dry benzene were added, drop-by-drop and at room-temperature, 5 g of propionyl chloride. The mixture was heated to 90° C. for 5 hours and then poured into water. The benzene fraction was separated out and washed first with a diluted solution of sodium hydroxide and then with diluted hydrochloric acid. The organic phase was dried over magnesium sulphate and evaporated under vacuum.

In this manner, 7 g of N-propionyl-1,1-di-n-propyl-n-butylamine were obtained after recrystallization from acetone. This product was in the form of colourless crystals.

M.P.: 96° C.
Yield: 66%

(b) N-n-Propyl-1,1-di-n-propyl-n-butylamine hydrochloride

To a suspension of 0.760 g (0.02 mol) of lithium aluminium hydride in 50 ml of anhydrous ethyl ether, were added 2.13 g (0.01 mol) of N-propionyl-1,1-di-n-propyl-n-butylamine, prepared as described hereabove. The mixture was heated under reflux for 3 hours and then hydrolysed by adding ice. The ethereal fraction was separated out, washed twice with a 10%-hydrochloric acid solution and dried over magnesium sulphate. The desired hydrochloride was then precipitated by adding gaseous hydrogen chloride.

In this manner, 1.5 g of N-n-propyl-1,1-di-n-propyl-n-butylamine hydrochloride were obtained after recrystallization from acetonitrile. This product was in the form of colourless crystals.

M.P.: 223° C.
Yield: 65%

EXAMPLE 18

Preparation of N-isopropyl-1,1-di-n-propyl-n-butylamine hydrochloride (a) N-Isopropyl-1,1-di-n-propyl-n-butylamine Into a flask, fitted with a condenser, were introduced 15.7 g (0.1 mol) of 1,1-di-n-propyl-n-butylamine, 20.4 g (0.12 mol) of isopropyl iodide and 10.1 g (0.12 mol) of sodium bicarbonate.

While stirring, the mixture was heated by means of an oil-bath maintained at 140° C. for 72 hours. The precipitate so obtained was filtered out and washed twice with ether. After evaporation of the solvent, the oil so obtained was distilled using a spinning band column.

In this manner, 7.8 g of N-isopropyl-1,1-di-n-propyl-n-butylamine were obtained in the form of a colourless liquid.

B.P.: 85° C. under 9 mm Hg
Yield: 40%

(b) N-Isopropyl-1,1-di-n-propyl-n-butylamine hydrochloride

In 100 ml of ethanol were dissolved 6 g of the amine previously prepared and the solution so obtained was treated with 3 ml of concentrated hydrochloric acid. The solution was evaporated to dryness and the desired hydrochloride was precipitated by adding 100 ml of isopropyl ether. The hydrochloride in question was then purified by sublimation under 1 mm Hg at a temperature of 210° C.

In this manner, 4.8 g of N-isopropyl-1,1-di-n-propyl-n-butylamine hydrochloride were obtained in the form of colourless crystals.

M.P.: 197° C. (sublimation)
Yield: 68%

EXAMPLE 19

Preparation of N-allyl-1,1-di-n-propyl-n-butylamine hydrochloride (a) N-Allyl-1,1-di-n-propyl-n-butylamine A mixture constituted by 12.1 g of allyl bromide, 25 g of sodium bicarbonate, 250 ml of ethanol and 19.35 g (0.1 mol) of 1,1-di-n-propyl-n-butylamine hydrochloride was refluxed for 48 hours. After separation of the insoluble fraction, the ethanol was evaporated out under vacuum and the oil so obtained was treated with 50 ml of a 10%-sodium hydroxide solution and 200 ml of ether. The organic phase was separated out and distilled under reduced pressure.

In this manner, 9 g of N-allyl-1,1-di-n-propyl-n-butylamine were obtained in the form of a slightly coloured liquid.

B.P.: 116° C. under 20 mm Hg
Yield: 89%

(b) N-Allyl-1,1-di-n-propyl-n-butylamine hydrochloride

By bubbling dry gaseous hydrogen chloride through an ethereal solution of the amine so prepared, the desired hydrochloride was precipitated and then filtered out and dried.

In this manner, N-allyl-1,1-di-n-propyl-n-butylamine hydrochloride was obtained in the form of colourless crystals.

M.P.: 194°–195° C.
Quantitative yield.

EXAMPLE 20

Preparation of
N-propargyl-1,1-di-n-propyl-n-butylamine
hydrochloride (a) N-Propargyl-1,1-di-n-propyl-n-butylamine Over a period of 48 hours, a mixture constituted by 11.9 g (0.1 mol) of propargyl bromide, 25 g of sodium bicarbonate, 250 ml of ethanol and 19.7 g (0.1 mol) of 1,1-di-n-propyl-n-butylamine was refluxed. After the insoluble fraction was filtered out and the ethanol evaporated off, the mixture was treated by means of a diluted solution of sodium hydroxide. The organic phase was extracted with ether and distilled using a spinning band column.

In this manner, 10 g of N-propargyl-1,1-di-n-propyl-n-butylamine were isolated in the form of a pale yellow liquid.

B.P.: 94°–96° C. under 5 mm Hg
Yield: 51%

(b) N-Propargyl-1,1-di-n-propyl-n-butylamine hydrochloride

By bubbling dry and gaseous hydrochloric acid through an ethereal solution of the amine so obtained, the desired hydrochloride was precipitated and was then filtered out and dried.

In this manner, N-propargyl-1,1-di-n-propyl-n-butylamine hydrochloride was obtained in the form of crystals.

M.P.: 154°–155° C.
Quantitative yield.

By following the same procedure as that described hereabove but using the appropriate starting-products, the compound hereunder was prepared:

| Compound | M.P. °C. |
|---|---|
| N-Methyl-1,1-di-n-propyl-n-butylamine hydrochloride | 133–134 |

EXAMPLE 21

Preparation of
N,N-dipropargyl-1,1-di-n-propyl-n-butylamine
hydrochloride (a) N,N-Dipropargyl-1,1-di-n-propyl-n-butylamine By continuing the distillation operation commenced in the above Example 20 (a) with a view to obtaining N-propargyl-1,1-di-n-propyl-n-butylamine, the corresponding N,N-dipropargyl derivative was isolated.

In this manner, 3 g of N,N-dipropargyl-1,1-di-n-propyl-n-butylamine were obtained in the form of a colourless liquid.

B.P.: 120° C. under 5 mm Hg
Yield: 13%

(b) N,N-Dipropargyl-1,1-di-n-propyl-n-butylamine hydrochloride

By bubbling dry gaseous hydrogen chloride through an ethereal solution of the amine thus obtained, the desired hydrochloride was precipitated.

In this manner, N,N-dipropargyl-1,1-di-n-propyl-n-butylamine hydrochloride was obtained in the form of colourless crystals.

M.P.: 177° C. (decomposition)

By following the same procedure as that described above but using the appropriate starting-products, the compound hereunder was prepared:

| Compound | M.P. °C. |
|---|---|
| N,N-Dimethyl-1,1-di-n-propyl-n-butylamine hydrochloride | 228–229 |

EXAMPLE 22

Preparation of
N,N-dimethyl-1,1-di-n-propyl-n-butylamine
hydrochloride (a) N,N-Dimethyl-1,1-di-n-propyl-n-butylamine Over a period of 6 hours, 40 ml of a 30%-solution of formic aldehyde and 15.7 g (0.01 mol) of 1,1-di-n-propyl-n-butylamine, were heated under reflux. After this operation, 40 ml of pure formic acid were added and heating was maintained for 7 hours. After the solution was concentrated, the oil so obtained was treated with a diluted and iced solution of sodium hydroxide. The organic fraction was extracted with ether, dried over magnesium sulphate, concentrated under vacuum and distilled under reduced pressure.

In this manner, 16 g of N,N-dimethyl-1,1-di-n-propyl-n-butylamine were collected in the form of a colourless liquid.

B.P.: 96°–97° C. under 15 mm Hg
Yield: 86%

(b) N,N-Dimethyl-1,1-di-n-propyl-n-butylamine hydrochloride

By bubbling gaseous dry hydrogen chloride through an ethereal solution of the amine previously obtained, the desired hydrochloride was precipitated.

In this manner, N,N-dimethyl-1,1-di-n-propyl-n-butylamine hydrochloride was obtained in the form of colourless crystals.

M.P.: 228°–229° C. (with sublimation)
Quantitative yield.

EXAMPLE 23

Preparation of
N,N-dimethyl-1-n-propyl-1-isobutyl-n-butylamine
hydrochloride (a) N,N-Dimethyl-1-n-propyl-1-isobutyl-n-butylamine In a two-necked flask, fitted with a mechanical stirrer and a condenser, was heated under reflux for 5 hours a mixture of 10 ml of a 30%-aqueous solution of formic aldehyde, 10 ml of formic acid and 10.7 g (0.62 mol) of 1-n-propyl-1-isobutyl-n-butylamine. After that, 10 ml of fuming hydrochloric acid (d=1.19) were added to the cold solution which was then concentrated under partial vacuum. The residual oil so obtained was then treated with 100 ml of distilled water and 30 ml of a sodium hydroxide solution (d=1.38). The amine so obtained was extracted with ether and the organic fraction was distilled under reduced pressure.

In this manner, 7.25 g of N,N-dimethyl-1-n-propyl-1-isobutyl-n-butylamine was isolated in the form of a colourless liquid.

B.P.: 106°–107° C. under 17 mm Hg
Yield: 57%

(b) N,N-Dimethyl-1-n-propyl-1-isobutyl-n-butylamine hydrochloride

By adding concentrated hydrochloric acid to an ethanolic solution of the amine previously obtained, the desired hydrochloride was precipitated, crystallized in isopropyl ether and then recrystallized from methylethylketone.

In this manner, N,N-dimethyl-1-n-propyl-1-isobutyl-n-butylamine hydrochloride was obtained in the form of colourless crystals.

M.P.: 186°–187° C.
Yield: 60%

EXAMPLE 24

Preparation of
N-ethyl-N-methyl-1,1-di-n-propyl-n-butylamine hydrochloride (a) N-Ethyl-N-methyl-1,1-di-n-propyl-n-butylamine Over a period of 5 hours, a mixture of 11.3 g (0.061 mol) of N-ethyl-1,1-di-n-propyl-n-butylamine, 10 ml of a 30%-aqueous solution of formic aldehyde and 9.4 ml of formic acid was refluxed. To the reaction medium was added 10 ml of concentrated and iced hydrochloric acid and the solution was then concentrated under vacuum. The oil so obtained was taken up with 100 ml of water and 30 ml of a concentrated sodium hydroxide solution. The organic fraction was extracted with ether and distilled under reduced pressure using a spinning band column.

In this manner, 10 g of N-ethyl-N-methyl-1,1-di-n-propyl-n-butylamine were isolated in the form of a colourless liquid.

B.P.: 92° C. under 11 mm Hg
Yield: 83%

(b) N-Ethyl-N-methyl-1,1-di-n-propyl-n-butylamine hydrochloride

To a solution of 7 g (0.035 mol) of the amine previously obtained, were added 5 ml of concentrated hydrochloric acid. The solution was concentrated to dryness and the oil so obtained was taken up with 50 ml of isopropyl ether. The precipitate was separated out and dried under vacuum at 50° C. in the presence of phosphoric anhydride and potassium hydroxide. The dry product so obtained was then recrystallized from 100 ml of methylethylketone.

In this manner, 5 g of N-ethyl-N-methyl-1,1-di-n-propyl-n-butylamine hydrochloride were obtained in the form of colourless crystals which sublimated at about 200° C.

Yield: 61%

EXAMPLE 25

Preparation of
N-(2-hydroxyethyl)-1,1-di-n-propyl-n-butylamine hydrochloride (a) Ethyl 2-(1,1-di-n-propyl-n-butylamino)-ethanoate Into a 500-ml three-necked flask fitted with a mechanical stirrer and a condenser, were introduced 23.6 g (0.15 mol) of 1,1-di-n-propyl-n-butylamine, 16.8 g of sodium bicarbonate and 300 ml of ethanol. To this mixture were then added 28.4 g (0.17 mol) of ethyl bromoacetate and, while stirring the whole was refluxed for 20 hours. After this operation, 200 ml of ether were added and the precipitate which formed was separated out. The solution was concentrated and the oil so obtained was distilled under reduced pressure.

In this manner, 22.9 g of ethyl 2-(1,1-di-n-propyl-n-butylamino)-ethanoate were obtained.

B.P.: 90°–92° C. under 0.3 mm Hg
Yield: 63%

(b) N-(2-Hydroxyethyl)-1,1-di-n-propyl-n-butylamine

To a suspension of 7.6 g (0.2 mol) of lithium aluminium hydride in 15 ml of ether, were added 22.8 g (0.094 mol) of ethyl 2-(1,1-di-n-propyl-n-butylamino)-ethanoate dissolved in 50 ml of ether. The mixture was heated under reflux for 20 hours and then while cold, hydrolyzed by adding ice. The precipitate so obtained was filtered out, washed with ether and the solvent was evaporated off under vacuum.

In this manner, 17.8 g of N-(2-hydroxyethyl)-1,1-di-n-propyl-n-butylamine were obtained.

Yield: 94%

(c) N-(2-Hydroxyethyl)-1,1-di-n-propyl-n-butylamine hydrochloride

To a solution of 3.75 g (0.0187 mol) of the amine previously obtained in 150 ml of ethanol, were added 1.9 ml of concentrated hydrochloric acid. After the solvent was eliminated under vacuum, the oil so obtained was taken up with 100 ml of isopropyl ether. The desired hydrochloride, which precipitated, was separated out and then recrystallized from 150 ml of ethyl acetate.

In this manner, 2.7 g of N-(2-hydroxyethyl)-1,1-di-n-propyl-n-butylamine hydrochloride were obtained.

M.P.: 157° C.
Yield: 60%

EXAMPLE 26

Preparation of
N-(3-oxapentamethylene)-1,1-di-n-propyl-n-butylamine hydrochloride or tri-n-propylmethylmorpholine hydrochloride (a) N-(3-Oxapentamethylene)-1,1-di-n-propyl-n-butylamine Under vigorous stirring, a mixture of 39 g (0.25 mol) of 1,1-di-propyl-n-butylamine, 40 g of di-(2-chloroethyl) oxide and 26.5 g of sodium carbonate was refluxed for five days. The mixture was treated with water and the organic fraction was extracted with ether. The organic phase was dried over magnesium sulphate evaporated under vacuum and distilled under reduced pressure.

In this manner, 25 g of N-(3-oxapentamethylene)-1,1-di-n-propyl-n-butylamine were collected in the form of colourless liquid.

B.P.: 105°–106° C. (under 5 mm Hg)
Yield: 44%

(b) N-(3-Oxapentamethylene)-1,1-di-n-propyl-n-butylamine hydrochloride

A solution of 3 g of N-(3-oxapentamethylene)-1,1-di-n-propyl-n-butylamino, previously obtained, in 15 ml of isopropanol was treated with 1.5 ml of concentrated hydrochloric acid (d=1.19) and the desired hydrochloride was precipitated by adding 25 ml of isopropyl ether.

In this manner, N-(3-oxapentamethylene)-1,1-di-n-propyl-n-butylamine hydrochloride was obtained in the form of brillant and colourless crystals which sublimated between 140° and 150° C.

Yield: 80%

EXAMPLE 27

Preparation of
N,N-ethylene-1,1-di-n-propyl-n-butylamine

In a 250-ml three-necked flask containing 15 g (0.063 mol) of N-(2-hydroxyethyl)-1,1-di-n-propyl-n-butylamine hydrochloride, prepared as described hereabove, were slowly added, while stirring, 15 ml of freshly distilled chlorosulphonic acid. During the operation of addition, a strong exothermic reaction was observed. The mixture was further heated to 80° C. and using a water pump, a partial vacuum was created in the flask. Under these conditions, heating was maintained at 80° C. for one hour and then, at atmospheric pressure the mixture was heated at 140° C. for 90 minutes. The viscous mixture was stirred for 12 hours with 100 ml of distilled water and then poured into a flask containing 300 ml of water and 100 ml of a sodium hydroxide solution. The mixture was then submitted to steam distillation and 500 ml of distillate were collected. After 100 ml of a sodium hydroxide solution were added, the basic fraction of the distillate was extracted with ether. The ether was evaporated off under vacuum and the residual oil was distilled.

In this manner, 8.7 g of N,N-ethylene-1,1-di-n-propyl-n-butylamine were isolated in the form of a colourless liquid.

B.P.: 103°–104° C. under 18 mm Hg
Yield: 76%

EXAMPLE 28

Preparation of
N-(3-hydroxy-n-propyl)-1,1-di-n-propyl-n-butylamine hydrochloride (a) Methyl 3-(1,1-di-n-propyl-n-butylamino)-propanoate A solution of 28.4 g (0.33 mol) of methyl acrylate in 60 ml of methanol was heated under reflux for 48 hours together with 47.1 g (0.3 mol) of 1,1-di-n-propyl-n-butylamine. After the methanol was eliminated under vacuum, the liquid so obtained was distilled.

In this manner, 61 g of methyl 3-(1,1-di-n-propyl-n-butylamino)-propanoate were obtained.

B.P.: 97°–98° C. under 0.4 mm Hg
Yield: 82%

(b) N-(3-Hydroxy-n-propyl)-1,1-di-n-propyl-n-butylamine

Into a 500-ml three-necked flask fitted with a mechanical stirrer, a condenser and a dropping-funnel were introduced 3.8 g (0.17 mol) of lithium aluminium hydride and 130 ml of dry ether. To this mixture were slowly added 12.2 g (0.05 mol) of methyl 3-(1,1-di-n-propyl-n-butylamino)-propanoate, prepared as previously described. The reaction medium was heated under reflux for 12 hours and then hydrolyzed. The precipitate which formed was washed with ether, the ether was evaporated off and the oil so obtained was distilled.

In this manner, 14.9 g of N-(3-hydroxy-n-propyl)-1,1-di-n-propyl-n-butylamine were collected in the form of a colourless liquid.

B.P.: 107°–108° C. under 0.4 mm Hg
Yield: 85%

(c) N-(3-Hydroxy-n-propyl)-1,1-di-n-propyl-n-butylamine hydrochloride

A solution of 10.2 g of the amine previously obtained in 150 ml of ethanol was treated with 5 ml of concentrated hydrochloric acid. The solution was concentrated to dryness and the oil so obtained was taken up with 100 ml of isopropyl ether. The precipitate which formed was separated out and recrystallized from 120 ml of ethyl acetate.

In this manner, 11.25 g of N-(3-hydroxy-n-propyl)-1,1-di-n-propyl-n-butylamine hydrochloride were obtained.

M.P.: 121°–122° C.
Yield: 90%

EXAMPLE 29

Preparation of
N,N-trimethylene-1,1-di-n-propyl-n-butylamine hydrochloride (a) N,N-Trimethylene-1,1-di-n-propyl-n-butylamine Into a 500-ml three-necked flask, fitted with a mechanical stirrer, a dip thermometer, a dropping-funnel and a calcium chloride trap, were introduced 18.3 g (0.07 mol) of triphenylphosphine, 150 ml of acetonitrile and 50 ml of ethyl ether. The mixture was cooled to 0° C. and then 11.2 g (0.07 mol) of bromine were added, drop-by-drop and while stirring. After this operation, a solution of 14 g (0.065 mol) of N-(3-hydroxy-n-propyl)-1,1-di-n-propyl-n-butylamine in 25 ml of acetonitrile was first added followed by 19.4 ml (0.14 mol) of anhydrous triethylamine while maintaining the reaction medium at a temperature of about 0° C. The mixture was allowed to stand for 12 hours at room temperature and the precipitate which formed was separated out and washed with ether. To the filtrate, 100 ml of water and 30 ml of concentrated hydrochloric acid were added and the solvents were evaporated out under vacuum. The precipitate was filtered off and washed first with 5%-hydrochloric acid and then with water.

From the aqueous solution, made alkaline by adding sodium hydroxide, the organic fraction was continuously extracted for 48 hours with methylene chloride. The solvent was eliminated and the residue was distilled under reduced pressure.

In this manner, N,N-trimethylene-1,1-di-n-propyl-n-butylamine was obtained in the form of a colourless liquid.

B.P.: 112°–115° C. under 14 mm Hg
Yield: 57%

(b) N,N-Trimethylene-1,1-di-n-propyl-n-butylamine hydrochloride

A solution of 6.9 g of the amine, previously obtained, in dry ether, was treated with ether saturated with gaseous hydrogen chloride to pH 3 to 4. The precipitate was separated out, washed with ether and dried.

In this manner, N,N-trimethylene-1,1-di-n-propyl-n-butylamine hydrochloride was obtained in the form of colourless crystals.

M.P.: 92°–93° C.
Yield: 87%

EXAMPLE 30

Preparation of
N-methylene-1,1-di-n-propyl-n-butylamine

Into a 1-liter three-necked flask, equipped with a mechanical stirrer and a Dean Stark apparatus fitted with a condenser, were introduced 300 ml of benzene, 120 ml of a 30%-solution of formic aldehyde and 11 g (0.07 mol) of 1,1-di-n-propyl-n-butylamine. The mixture was heated on an oil-bath to eliminate the water by azeotropic distillation, the benzene solution was evaporated to dryness and the oil so obtained was distilled.

In this manner, 11 g of N-methylene-1,1-di-n-propyl-n-butylamine were obtained in the form of a colourless liquid.

B.P.: 85° C. under 13 mm Hg

EXAMPLE 31

Preparation of
N-(2-hydroxyethyl)-1,1-di-n-propyl-n-butylamine hydrochloride

In a 50-ml flask fitted with several inlet tubes, a mechanical stirrer, a condenser for reflux, a thermometer and a dip tube for allowing the entry of nitrogen or ethylene oxide, was introduced 0.2 ml of boron trifluoride in the form of etherate and 10 g of 1,1-di-n-propyl-n-butylamine. The apparatus was cleared with nitrogen and the reaction medium was heated, while stirring, to 160° C. by means of an oil-bath. After that, ethylene oxide was continuously bubbled through the reaction medium for 4 hours, care being taken to maintain the reaction temperature at 180°–200° C. The flask was cleared with nitrogen before cooling and the reaction mixture was acidified with 20 ml of 36%-hydrochloric acid. After cooling to 0° C., the mixture was maintained at this temperature for 2 hours and then suction-filtered and dried to constant weight.

In this manner, 5 g of N-(2-hydroxyethyl)-1,1-di-n-propyl-n-butylamine hydrochloride were obtained.
M.P.: 175° C.

EXAMPLE 32

Preparation of
N,N-bis-(2-hydroxyethyl)-1,1-di-n-propyl-n-butylamine hydrochloride In an enamelled bomb-apparatus fitted with a dip-thermometer, a manometer, an adjusted safety valve, were introduced at low temperature, 48.6 g (60 ml) of methanol, 74.8 g (84 ml) (0.85 mol) of liquid ethylene oxide, 2.5 g of 36%-hydrochloric acid and 25 g (0.159 mol) of 1,1-di-n-propyl-n-butylamine. The bomb-apparatus was closed, cleared with nitrogen and immersed in a water-bath thermostated at 50°±2° C. (pressure about 2.8 bars). The reaction was maintained for 40 hours and then the pressure was lowered to atmospheric pressure. The apparatus was cleared with nitrogen and the reaction medium was concentrated in a rotary evaporator to constant weight (45 g). The oil so obtained was taken up with 300 ml of ethyl ether and the ethereal solution was washed with 50 ml of a 4%-aqueous solution of sodium hydroxide and then with water. The organic fraction was dried over anhydrous sodium sulphate and then evaporated to dryness to obtain 39 g of an oil which crystallized at about 50° C. This solid was recrystallized by dissolving in 160 ml of heptane under reflux, suction-filtered after 2 hours at −5° C. and dried to constant weight.

In this manner, 34 g of N,N-bis-(2-hydroxyethyl)-1,1-di-n-propyl-n-butylamine hydrochloride were obtained.
M.P.: 64° C.
Yield: 87%

EXAMPLE 33

Preparation of
N-(3-Oxapentamethylene)-1,1-di-n-propyl-n-butylamine hydrochloride (a) N-2-Morpholino-2-n-propyl-valeronitrile A solution of 43.5 g (0.5 mol) of morpholine in 200 ml of methanol was treated with 40 ml of iced and concentrated hydrochloric acid. To the solution of morpholine hydrochloride so obtained were added 57 g (0.5 mol) of di-n-propyl ketone and 100 ml of methanol and the resulting mixture was added to a suspension of 36 g of potassium cyanide in 400 ml of methanol. The reaction medium was stirred for 3 hours at room-temperature and then heated to 50° C. for 12 hours. The precipitate which formed was filtered out, the methanol was evaporated off under vacuum and the oil so obtained was taken up with 100 ml of distilled water. The organic phase was extracted with ether, the ether was evaporated off and the residue was distilled under reduced pressure.

In this manner, N-2-morpholino-2-n-propyl-valeronitrile was obtained in the form of a colourless liquid.
Yield: 17%
B.P.: 137°–140° C. (under 3.5 mm Hg)

(b) N-(3-Oxapentamethylene)-1,1-di-n-propyl-n-butylamine

To a solution of propyl magnesium bromide, prepared from 1.1 g of magnesium turnings, from 5.6 g of propyl bromide and from 60 ml of dry ethyl ether, were added at room-temperature and while stirring, 8.4 g (0.04 mol) of 2-N-morpholino-2-n-propyl-valeronitrile previously obtained, in 30 ml of anhydrous ether.

The reaction mixture was refluxed for 2 hours and then, while cold, 30 ml of distilled water were added. The ether was separated out, dried over magnesium sulphate and evaporated off under vacuum. The resulting residue was distilled under reduced pressure.

In this manner, N-(3-oxapentamethylene)-1,1-di-n-propyl-n-butylamine was obtained.
Yield: 65%
B.P.: 96°–97° C. (under 4 mm Hg)

(c) N-(3-Oxapentamethylene)-1,1-di-n-propyl-n-butylamine hydrochloride

A solution of 4.5 g of N-(3-oxapentamethylene)-1,1-di-n-propyl-n-butylamine in 23 ml of isopropanol was treated with 2.3 ml of concentrated hydrochloric acid (d=1.19). By adding 37.5 ml of isopropyl ether, the desired hydrochloride was precipitated.

In this manner, N-(3-oxapentamethylene)-1,1-di-n-propyl-n-butylamine hydrochloride was obtained. Sublimation: between 140° and 150° C.

EXAMPLE 34

Preparation of
N-(3-oxapentamethylene)-1,1-di-n-propyl-n-butylamine hydrochloride (a) N-(3-Oxapentamethylene)-1,1-di-n-propyl-n-butylamine A solution of 5 g (about 0.02 mol) of N,N-bis-(2-hydroxyethyl)-1,1-di-n-propyl-n-butylamine, prepared as previously described, in 50 ml of benzene was heated under reflux for 5 hours in the presence of 5.6 g (0.04 mol) of phosphoric anhydride. The mixture was stirred with 20 ml of distilled water and then separated from the aqueous phase which was treated with a diluted solution of sodium hydroxide and further extracted with ether.

In this manner, N-(3-oxapentamethylene)-1,1-di-n-propyl-n-butylamine was obtained.

B.P.: 256° C. (under 750 mm Hg)

(b) N-(3-Oxapentamethylene)-1,1-di-n-propyl-n-butylamine hydrochloride

A solution of 4 g of N-(3-oxapentamethylene)-1,1-di-n-propyl-n-butylamine in 20 ml of isopropanol was treated with 2 ml of concentrated hydrochloric acid (d=1.19) and then 33 ml of isopropyl ether were added.

In this manner, N-(3-oxapentamethylene)-1,1-di-n-propyl-n-butylamine hydrochloride was obtained which sublimated between 140° and 150° C.

EXAMPLE 35

A hard-gelatin capsule containing the following ingredients was prepared in accordance with known pharmaceutical techniques:

| Ingredients | mg |
|---|---|
| 1,1-Di-n-propyl-n-butylamine hydrochloride | 5 |
| Milk sugar | 45 |
| | 50 |

We claim:
1. A methylamine derivative corresponding to the formula:

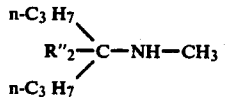

or a pharmaceutically acceptable acid addition salt thereof, wherein R"$_2$ represents n-propyl, isopropyl, isobutyl or allyl.

2. N-Methyl-1,1-di-n-propyl-n-butylamine or a pharmaceutically acceptable acid addition salt thereof.

3. N-Methyl-1-n-propyl-1-isopropyl-n-butylamine or a pharmaceutically acceptable acid addition salt thereof.

4. N-Methyl-1-n-propyl-1-isobutyl-n-butylamine or a pharmaceutically acceptable acid addition salt thereof.

5. N-Methyl-1-n-propyl-1-allyl-n-butylamine or a pharmaceutically acceptable acid addition salt thereof.

6. A methylamine derivative according to any preceding claim wherein the pharmaceutically acceptable acid addition salt is the hydrochloride.

* * * * *